United States Patent
McBeth et al.

(10) Patent No.: US 12,121,545 B2
(45) Date of Patent: Oct. 22, 2024

(54) COMPOSITION FOR A FECAL-DERIVED STERILIZED POSTBIOTIC IN ANTI-AGING AND NEUROTHERAPEUTIC APPLICATIONS

(71) Applicant: THAENA INC., Vancouver, WA (US)

(72) Inventors: Andrea McBeth, Portland, OR (US); Piper Dobner, Milwaukie, OR (US); Brice Thompson, Portland, OR (US)

( * ) Notice: Subject to any disclaimer, the term of this patent is extended or adjusted under 35 U.S.C. 154(b) by 0 days.

(21) Appl. No.: 18/228,222

(22) Filed: Jul. 31, 2023

(65) Prior Publication Data

US 2024/0033299 A1 Feb. 1, 2024

Related U.S. Application Data

(60) Provisional application No. 63/394,016, filed on Aug. 1, 2022.

(51) Int. Cl.
*A61K 35/38* (2015.01)
(52) U.S. Cl.
CPC .................... *A61K 35/38* (2013.01)
(58) Field of Classification Search
CPC ...................................... A61K 35/38
See application file for complete search history.

(56) References Cited

U.S. PATENT DOCUMENTS

2023/0089315 A1 3/2023 McBeth

FOREIGN PATENT DOCUMENTS

WO WO-2021076999 A1 * 4/2021 ............ A61K 31/19
WO 2022/232661 A1 11/2022

OTHER PUBLICATIONS

Wikipedia, Cetyl Alcohol, accessed on Mar. 2, 2024, pp. 1-3 (Year: 2024).*

* cited by examiner

*Primary Examiner* — Qiuwen Mi
(74) *Attorney, Agent, or Firm* — Caldwell Intellectual Property Law

(57) ABSTRACT

A composition and a method for analyzing an anti-aging effect of the composition of a fecal derived sterilized postbiotic are disclosed. The method includes obtaining a baseline biomarker of aging measurement, wherein the baseline biomarker of aging measurement includes a biomarker of aging, selecting a dose schedule from a plurality of dose schedules of a composition for a fecal derived sterilized postbiotic as a function of the baseline biomarker of aging measurement, wherein the composition includes a plurality of biological macromolecules including at least a short chain fatty acid, wherein the short chain fatty acid includes acetic acid, propionic acid, and butyric acid and a plurality of agents, wherein the plurality of agents is configured to regulate the biomarker of aging and administering the composition to a subject.

19 Claims, 15 Drawing Sheets

| Table 500 |
|---|
| Telomere Length 504 |
| C-reactive protein 508 |
| Small Dense LDL Particles 512 |
| Homocysteine 516 |
| Hemoglobin A1C 520 |
| Vitamin D 524 |
| Fasting Insulin 528 |
| Immunological Tests 532 |
| mTOR activity 536 |
| Insulin-like Growth Factors 540 |
| 5' AMP-activated Protein Kinase 544 |
| Heart Rate Variability 548 |
| Blood Glucose 552 |
| DNA Methylation 556 |
| Whole-Genome Sequencing 560 |
| Metabolomics 564 |
| Redox Potential 568 |
| Quantitative Electro-encephalography 572 |
| Validated Questionnaires 576 |
| Smart Device Data 580 |

*FIG. 5*

| Table 600 | Amyloid beta 604 | B-site APP-cleaving Enzyme 1 Gene 608 | Soluble AB Precursor Protein 612 | Autoantibodies 616 | Cerebrospinal Fluid Biomarkers 620 |
|---|---|---|---|---|---|

*FIG. 6*

COMPOSITION FOR A FECAL-DERIVED STERILIZED POSTBIOTIC IN ANTI-AGING AND NEUROTHERAPEUTIC APPLICATIONS

CROSS-REFERENCE TO RELATED APPLICATIONS

This application claims the benefit of priority of U.S. Provisional Patent Application Ser. No. 63/394,016 filed on Aug. 1, 2022, and titled "COMPOSITION FOR A FECAL-DERIVED STERILIZED POSTBIOTIC IN ANTI-AGING AND NEUROTHERAPEUTIC APPLICATIONS," which is incorporated by reference herein in its entirety.

FIELD OF THE INVENTION

The present invention generally relates to the field of postbiotics. In particular, the present invention is directed to a composition for a fecal-derived sterilized postbiotic in anti-aging and neurotherapeutics.

BACKGROUND

Large scale clinical research specifically designed to address safety and tolerability of non-sterilized fecal microbiota transplant (FMT) in healthy populations has been lacking, which may be in part due to the financial burden of these studies and to the speed with which the non-sterilized FMT was introduced. However, the efficacy of non-sterilized FMT in treating *Clostridioides difficile* infections and related conditions allowed non-sterilized FMT has not been adequately examined.

SUMMARY OF THE DISCLOSURE

In an aspect, a method for analyzing an anti-aging effect of composition of a fecal derived sterilized postbiotic is disclosed. The method includes obtaining a baseline biomarker of aging measurement, wherein the baseline biomarker of aging measurement includes a biomarker of aging, selecting a dose schedule from a plurality of dose schedules of a composition for a fecal derived sterilized postbiotic as a function of the baseline biomarker of aging measurement, wherein the composition includes a plurality of biological macromolecules including at least a short chain fatty acid, wherein the short chain fatty acid includes acetic acid, propionic acid, and butyric acid and a plurality of agents, wherein the plurality of agents is configured to regulate the biomarker of aging and administering the composition to a subject.

In another aspect, a composition for a fecal derived sterilized postbiotic for anti-aging is disclosed. The composition includes a plurality of dose schedules, wherein a dose schedule of the plurality of does schedules of is selected as a function of a baseline biomarker of aging measurement to be administered to a subject, wherein the baseline biomarker of aging measurement includes a biomarker of aging, a plurality of biological macromolecules including at least a short chain fatty acid, wherein the short chain fatty acid includes acetic acid, propionic acid, and butyric acid and a plurality of agents, wherein the plurality of agents is configured to regulate the biomarker of aging.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5 illustrates an exemplary table listing baseline biomarkers of aging monitored with the use of a composition;

FIG. 6 illustrates an exemplary table listing baseline biomarkers of aging related to neurodegeneration monitored with the use of a composition;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to a method for analyzing an anti-aging effect of composition of a fecal derived sterilized postbiotic. The method includes obtaining a baseline biomarker of aging measurement, wherein the baseline biomarker of aging measurement includes a biomarker of aging, selecting a dose schedule from a plurality of dose schedules of a composition for a fecal derived sterilized postbiotic as a function of the baseline biomarker of aging measurement, wherein the composition includes a plurality of biological macromolecules including at least a short chain fatty acid, wherein the short chain fatty acid includes acetic acid, propionic acid, and butyric acid and a plurality of agents, wherein the plurality of agents is configured to regulate the biomarker of aging and administering the composition to a subject.

For various medical reasons, it may be desirable to deliver healthy human stool and/or postbiotics extracted from stool to a recipient. The delivery of healthy human-derived stool to the colon of a recipient patient is generally known as fecal microbiota transplantation, microbial transfer therapy, or fecal transplant. In recent years, the transplant of healthy, live microbiota to a recipient has been useful for treating recurrent and/or antibiotic resistant infections.

The composition described herein involves a fecal-derived postbiotic product (also referred to herein as "FSP"). A FSP composition or extract is sterilized to exclude any live organisms (including, but not limited to, bacteria, archaea, fungi, parasites, protozoa, and viruses). Sterilized FSP and lyophilized sterilized FSP may be used to formulate various products. Dosages of each respectively can be about 0.25 milliliters to about 15 milliliters per day and about 10 milligrams to about 5 grams per day of a lyophilized FSP per subject. The sterilized FSP and lyophilized sterilized FSP may be formulated as appropriate for administration orally, intranasally, vaginally, rectally, or topically. The sterilized FSP and lyophilized sterilized FSP can be formulated into a capsule, soft gel, gummy soft gel, tablet, pill, gel, lotion, liquid or syrup, suppository, powder, mouthwash, and paste for purposes of administration. Exemplary embodiments illustrating aspects of the present disclosure are described below in the context of several specific examples.

Figure 1:
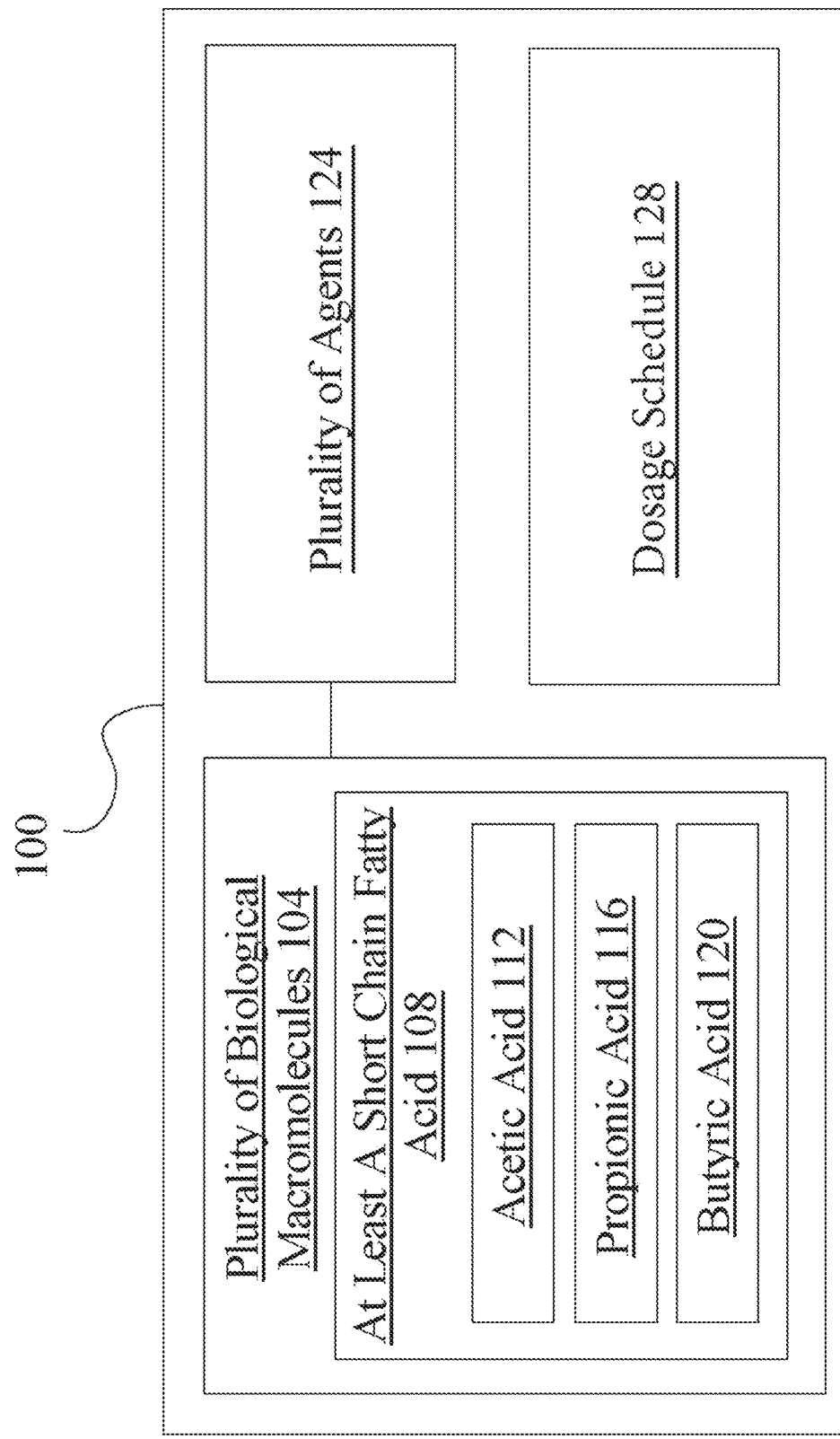
FIG. 1 illustrates a block diagram of an exemplary embodiment of a composition for a fecal derived sterilized postbiotic for anti-aging.

Referring now to FIG. 1, an exemplary embodiment of a composition for a fecal-derived sterilized postbiotic for anti-aging is illustrated. As used herein, "postbiotics" are chemicals released from microorganisms that live in a human or animal digestive tract when they metabolize precursor molecules originating from the host or from ingested foods. In an embodiment, a postbiotic may include a sterilized fecal-derived postbiotic composition or product containing said composition. For a non-limiting example, a postbiotic may at least include one or more biological macromolecules 104, cellular components of one or more killed bacteria, viruses, fungi, archaea, food byproducts, and/or donor-derived molecules. Short chain fatty acids (SCFAs) are an example of a primary bacterial metabolite. As used in this disclosure, a "metabolite" is a small molecule that is the intermediate or end product of metabolism. Composition 100 is "fecal-derived", which as used in this disclosure, is bodily matter derived from ingested food and the secretions of the intestines of living organisms. Fecal-derived matter may include but is not limited to, proteins, undigested food residues, polysaccharides, and microbial biomass. However, composition 100 is "sterilized" because it is free from bacteria or other living microorganisms. As used herein, the term "sterilize" means to remove or kill all bacteria, viruses, and other living organisms from a sample such as composition 100. The process of sterilization may include receiving a stool sample by collecting a plurality of samples from healthy donors who match a desired donor profile. Potential donors then may undergo a rigorous screening process to ensure safety and product quality. Once a donor is cleared, stool samples may then be collected, frozen, and stored at negative 20 degrees Celsius until manufacturing of composition 100 begins. As used in this disclosure, "anti-aging" refers to early detection, prevention, and treatment of age-related diseases (ARD). An "age-related disease," as used in this disclosure, is a disease that is seen with increasing frequency with increasing biological aging. They may be complications of biological aging. Anti-aging may include products and techniques slowing, preventing, or reversing the aging process and/or age-related diseases. Additionally and/or alternatively, additional disclosure related to composition 100 may be found in U.S. Nonprovisional application Ser. No. 17/721,908, filed on Apr. 15, 2022, and entitled "COMPOSITION OF MATTER AND METHODS FOR A FECAL-DERIVED STERILIZED PREBIOTIC AND POSTBIOTIC,", the entirety of which is incorporated herein by reference.

Still referring to FIG. 1, age-related diseases (ARD) may include age-related macular degeneration (AMD), a disease that affects the eyes and can lead to vision loss through break down of the central part of the retina called the macula. Degeneration can occur in one eye or both and can be classified as either wet (neovascular) or dry (atrophic). Wet AMD may be commonly caused by blood vessels near the retina that lead to swelling of the macula. The cause of dry AMD is less clear, but it is thought that it may be partly caused by breakdown of light-sensitive cells and tissue surrounding the macula. A major risk factor for AMD may include ages over 60. ARD may include Alzheimer's disease, a "protein misfolding" disease. Aging may cause mutations in protein folding, and as a result causes deposits of abnormal modified proteins accumulate in specific areas of the brain. In Alzheimer's, deposits of Beta-amyloid and hyperphosphorylated tau protein form extracellular plaques and extracellular tangles. These deposits may be neurotoxic and cause cognitive impairment due to their initiation of destructive biochemical pathways. ARD may include Atherosclerosis, an aging disease brought about by vascular remodeling, the accumulation of plaque, and the loss of arterial elasticity. Over time, these processes may stiffen the vasculature. For these reasons, older age may be listed as a major risk factor for atherosclerosis. Specifically, the risk of atherosclerosis may increase for men above 45 years of age and women above 55 years of age. ARD may include Benign prostatic hyperplasia (BPH), a noncancerous enlargement of the prostate gland due to increased growth. An enlarged prostate can result in incomplete or complete blockage of the bladder and interferes with a man's ability to urinate properly. Symptoms may include overactive bladder, decreased stream of urine, hesitancy urinating, and incomplete emptying of the bladder. By age 40, 10% of men will have signs of BPH and by age 60, this percentage increases by 5-fold. Men over the age of 80 have over a 90% chance of developing BPH and almost 80% of men will develop BPH in their lifetime. ARD may include cancer, most patients with invasive cancer are over 65.

Still referring to FIG. 1, in some embodiments, ARD may include but is not limited to adrenal fatigue, aging, allergies, food sensitivities, arthritis, asthma, autoimmune disease, cardiovascular disease, chronic fatigue syndrome, depression, anxiety, diabetes, eating disorders, fatigue, fibromyalgia, gastrointestinal disorders, high cholesterol, infertility, menopause, weight gain, obesity, infectious disease, neurological disease, gastroenterological disease, or the like.

Still referring to FIG. 1, in some embodiments, composition 100 may be configured to treat neurodegeneration. Neurodegeneration is further described below. As a non-limiting example, ARD may include Parkinson's disease, or simply Parkinson's, a long-term degenerative disorder of the central nervous system that mainly affects the motor system. The disease has many complications, including dementia, depression, anxiety. Parkinson's disease typically occurs in people over the age of 60, of whom about one percent are affected. The prevalence of Parkinson's disease dementia also increases with age, and to a lesser degree, duration of the disease. As another non-limiting example, ARD may include stroke and similar conditions. For the purposes of this disclosure, a "stroke" is a medical condition that occurs when the blood supply to a part of the brain is interrupted or reduced. Stroke may lead to the impairment of brain function. As another non-limiting example, ARD may include Huntington's disease, Alzheimer's disease, or the like.

Still referring to FIG. 1, composition 100 may be configured to improve oxidative stress tolerance, preserve mitochondrial function, support energy production, enhance cellular defense mechanisms against oxidative stress, stimulate endogenous antioxidants and enzymes, reduce oxidative stress and/or mitochondrial oxidative stress, improve mitochondrial function, improve healthspan, improve longevity, improve autophagy, increase autophagy, or the like. Oxidative stress and healthspan disclosed herein are further described below. For the purposes of this disclosure, "oxidative stress" is a physiological state characterized by an imbalance between the production of reactive oxygen species and the body's antioxidant defenses. In a non-limiting example, reactive oxygen species (ROS) can be generated endogenously as byproducts of cellular metabolism; for instance in the mitochondria. In another non-limiting example, ROS can be generated exogenously in the result of environmental pollutants, radiation, cigarette smoking, alcohol, certain foods, and drugs. In a healthy human, the body's antioxidant defenses can neutralize these molecules before they cause significant cellular damage. However, when their production overwhelms the body's capacity to neutralize and eliminate them, they can cause widespread cellular damage. Damage to cellular components, such as proteins, lipids, and DNA, can lead to functional impairment and cell death. Over time, the cumulative impact of oxidative stress can contribute to the aging process and the pathogenesis of numerous aging-related diseases (ARDs) as described in this disclosure. In another non-limiting example, oxidative stress can lead to chronic inflammation, further exacerbating tissue damage and promoting the generation of additional ROS. Composition 100 may include several biological compounds and metabolites that reduce oxidative stress, both systemically and within the microbiome. Acetate, hexanoate, and propionate can aid in maintaining cellular antioxidant defenses through energy production roles, while butyrate, isobutyrate, and isovalerate, as short-chain fatty acids, can modulate gene expression and cellular signaling. In a non-limiting example, essential amino acids and their derivatives like lysine, leucine, tyrosine, arginine, valine, citrulline, 2-methylbutyrate, and tryptophan may provide a multifaceted approach, aiding in tissue repair, protein synthesis, neurotransmitter synthesis, vasodilation, and enhancing cellular antioxidant defenses. In the microbiome, these metabolites, along with indole, indoleacetate, ornithine, lactate, thiamine, and choline may support a balanced and diverse microbial community, reduce inflammation, and optimize nutrient utilization. As described with respect to FIG. 4, composition 100 may improve oxidative stress tolerance in *Caenorhabditis elegans* in a dose-dependent manner. Compared to the vitamin C positive control and the DMSO negative control groups, even the lowest dosage of composition 100 may yield superior protection against exogenously-induced oxidative stress, as demonstrated by a significantly less average decline in the composition-treated nematodes. In a non-limiting example, the highest dosage group treated with 1.25 mg/mL of composition 100, showed an average decline of merely 3.2%, starkly less than the 25% average decline observed in the vitamin C control group. Thus, composition 100 may represent a potent protective agent against acute oxidative stress, underscoring the importance of these metabolites in combating oxidative stress.

Still referring to FIG. 1, for the purposes of this disclosure, "mitochondria" are organelles found within eukaryotic cells that produces energy. Mitochondria drives the production of adenosine triphosphate (ATP), the cell's primary energy currency, through a process known as oxidative phosphorylation which produce ROS as byproducts. In addition to energy production, mitochondria partake in calcium homeostasis, cell signaling, apoptosis (programmed cell death), and synthesis of specific biomolecules. Oxidative stress resulted by mitochondria function can instigate a damage to cellular components, for instance, mitochondrial DNA (mtDNA), proteins, and lipids. Damage to mtDNA can result in mutations that compromise the synthesis of proteins critical for oxidative phosphorylation, thus hampering mitochondrial function and triggering a cycle of ROS production (i.e. ROS-induced ROS release). In another non-limiting example, ROS can inflict lipid peroxidation damage to the mitochondrial membrane, impairing its integrity and function. It may induce the release of pro-apoptotic factors into the cytosol, triggering cell death. In a non-limiting example, preserving mitochondria function may prevent ARDs, cancer, disruptions in cellular signaling and processes, or the like.

Still referring to FIG. 1, composition 100 includes a plurality of biological macromolecules 104. In this disclosure, a "biological macromolecule," is a molecule ranging from 100 to 10,000 angstroms ($10^{-5}$ to $10^{-3}$ mm). A biological macromolecule may include molecules such as nucleic acids, proteins, carbohydrates, and lipids. Plurality of biological macromolecules 104 may include bile acids. A "bile acid," as used in this disclosure, is an acid made by the liver that is important for the digestion and absorption of fats. Plurality of biological macromolecules 104 may include amino acid derivatives. In this disclosure, "amino acid derivatives" are amino acid molecules that have had a reaction at the amino, carboxy, or side-chain functional groups or has had a hydrogen atom replaced by another heteroatom. Plurality of biological macromolecules 104 may further comprise ceramides. A "ceramide," as used in this disclosure, is a waxy lipid molecule found in cell membranes and composed of sphingosine and a fatty acid. Additionally, plurality of biological macromolecules 104 may further comprise lipopolysaccharides. "Lipopolysaccharides," as used in this disclosure, are large molecules consisting of a lipid and a polysaccharide composed of O-antigen, outer core and inner core joined by a covalent bond. Furthermore, plurality of biological macromolecules 104 may further comprise capsular polysaccharides. "Capsular polysaccharides," for the purposes of this disclosure, are highly hydrated molecules linked to a cell surface via covalent bonds to phospholipids. Lastly, plurality of biological macromolecules 104 may also include sphingosines, which as used in this disclosure, are unsaturated, long-chain amino alcohols. Sphingosines may be usually found in cell membranes. One or more of any of the biological macromolecules described above may be included in plurality of biological macromolecules 104. Examples of biological macromolecules may include, but without limitation, chenodeoxycholic acid, linoleic acid, deoxycholic acid, alanine, leucine, indole derivatives, palmitic acid, sugars, cis-vaccenic acid, 10-hydroxystearate, xenobiotics, nucleotides, or the like.

With continued reference to FIG. 1, plurality of macromolecules 104 may include a sugar. A "sugar," as used in this disclosure, is one or more carbohydrates. As non-limiting examples, a sugar may include a monosaccharide, a disaccharide, and/or an oligosaccharide. As non-limiting examples, a sugar may include glucose, fructose, galactose, sucrose, lactose, maltose and the like. Plurality of macromolecules 104 may include an amino acid. An "amino acid," as used in this disclosure, is an organic compound that contains an amino and carboxylate functional group along with a side chain specific to each particular amino acid. For instance, and without limitation, an amino acid may include histidine, isoleucine, leucine, lysine, methionine, phenylalanine, tryptophan, valine and the like. Plurality of macromolecules 104 may include a cofactor. A "cofactor" as used in this disclosure is a substance that aids in the activity of an enzyme. A cofactor may be a helper molecule that may assist in biochemical transformation. A cofactor may include an organic cofactor. For example, an organic cofactor may include a vitamin and/or vitamin derivative such as thiamine pyrophosphate, $NAD^+$, pyridoxal phosphate, methylcobalamin, biotin, Coenzyme A, ascorbic acid, menaquinone, flavin mononucleotide, and the like. In yet another non-limiting example, an organic cofactor may include a non-vitamin derivative such as adenosine triphosphate, S-Adenosyl methionine, Coenzyme B, Coenzyme M, Coenzyme Q, glutathione, heme, lipoamine, methanofuran, molybdopterin, nucleotide sugar, tetrahydrobioptrin and the like. A cofactor may include an inorganic cofactor. For example, an inorganic cofactor may include a metal ion such as iron, magnesium, manganese, cobalt, copper, zinc, molybdenum and the like. Plurality of macromolecules 104 may include a vitamin. A "vitamin," as used in this disclosure, is an organic molecule that is a micronutrient needed for functioning of an organism. A vitamin may be unable to be synthetized in sufficient amounts by an organism. A vitamin may include a mineral. For instance, and without limitation, a vitamin may include Vitamin A, Vitamin D, Vitamin E, Vitamin K, Vitamin C, Vitamin B6, Vitamin B12, folate, iodine, copper, zinc, and the like. Plurality of macromolecules 104 may include a preserving agent. A "preserving agent" as used in this disclosure, is any substance that aids in extending the shelf life or prevents undesirable chemical change of a composition. A preserving agent may include an antimicrobial preservative such as, but not limited to, sorbic acid, benzoic acid, parabens, sulfur dioxide, sulfites, nitrites, nitrates, lactic acid, propionic acid, phosphoric acid, formaldehyde and the like. A preserving agent may include an antioxidant such as but not limited to ascorbic acid, sodium ascorbate, butylated hydroxytoluene, gallic acid, sulfur dioxide, tocopherols and the like.

Continuing to refer to FIG. 1, plurality of biological macromolecules 104 include at least a short chain fatty acid (SCFAs) 108. In this disclosure, a "short chain fatty acid" is a fatty acid molecule with fewer than six carbon atoms. SCFAs represent a primary energy source for human or animal colonocytes, and as a result are important for gastrointestinal health. In some embodiments, at least a short chain fatty acid 108 may be considered a postbiotic, as described above, and may be produced by beneficial bacteria in a microbiome from carbohydrates and prebiotic dietary fibers. However, production of at least a short chain fatty acid 108 may be limited if the host does not consume enough plant-based foods or fiber or if certain SCFA-producing strains of bacteria are missing or deficient. Non-limiting examples of at least a short chain fatty acid 108 may be, without limitation, formic acid, acetic acid, propionic acid, butyric acid, isobutyric acid, valeric acid, and isovaleric acid, some of which are further explained below. At least a short chain fatty acid 108 may be in a salt formation. In this disclosure, "salt formation" refers to a form of acid that produces an acidic solution after dissolving in water. Acids may transform into salt formation when neutralized by metal carbonates. Also, at least a short chain fatty acid 108 may be in ester formation, which refers to a chemical compound derived from an acid in which at least one carboxyl group is replaced with a hydrocarbon group. Ester formation may occur as a function of a chemical reaction between carboxylic acids and alcohol. Any form of any of the at least a short chain fatty acids 108 explained above may be used in composition 100.

Still referring to FIG. 1, at least a short chain fatty acid 108 may include acetic acid 112. In this disclosure, "acetic acid" is an acidic, colorless liquid and organic compound with the chemical formula $CH_3COOH$. At least a short chain fatty acid 108 may also include propionic acid 116. A "propionic acid," as used in this disclosure, is a naturally occurring carboxylic acid with chemical formula $CH_3CH_2CO_2H$. Propionic acid 116 may be referred to as propionate or propanoate in its salt and ester formations, respectively. In addition, propionic acid 116 may be produced industrially by hydrocarboxylation of ethylene and may be miscible in water. At least a short chain fatty acid 108 may include butyric acid 120. As used in this disclosure, "butyric acid" is, is a straight-chain alkyl carboxylic acid with the chemical formula $CH_3CH_2CH_2CO_2H$ Butyric acid 120 may be an oily, colorless liquid with an unpleasant odor, or could be in salt and ester formation as well. In composition 100, the amount each of the above short chain fatty acids is represented by a specified ratio by weight. A "ratio by weight," as used in this disclosure, is a comparison of equal weights inside the composition, rather than by amount. Composition 100 may comprise a ratio by weight between acetic acid 112, propionic acid 116, and butyric acid 120, in which the ratio by weight may be within a range of 60±10: 20±10:20±10, respectively. As a non-limiting example, composition 100 may include acetic acid 112, propionic acid 116, and butyric acid 120 with a range of 60:20:20, respectively. As another non-limiting example, composition 100 may include acetic acid 112, propionic acid 116, and butyric acid 120 with a range of 70:15:15, respectively. As another non-limiting example, composition 100 may include acetic acid 112, propionic acid 116, and butyric acid 120 with a range of 50:25:25, respectively. As another non-limiting example, composition 100 may include acetic acid 112, propionic acid 116, and butyric acid 120 with a range of 50:30:20, respectively. Persons skilled in the art, upon reviewing the entirety of this disclosure, may appreciate various ratio of acetic acid 112, propionic acid 116, and butyric acid 120 for composition 100. Short chain fatty acids may be produced as an end-product of anaerobic fermentation of complex carbohydrates by the microbiota in the colon. Acetic acid 112 and butyric acid 120, explained below, may be essential or healthy human physiology because they are a primary energy source for colonocytes. Propionic acid, the other most abundant short chain fatty acid, may be utilized in the liver as a substrate for glucose production. Acetic acid, butyric acid and propionic acid can be generally represented in a ratio of 60:20:20. Short chain fatty acids may interact with a wide array of human cells and impact the immune system and metabolism throughout the body via G protein-coupled receptors (GPCRs). In addition, butyric acid 120 may act as a histone deacetylase inhibitor which impacts the epigenetics of human cells independent of GPCR signaling. These important postbiotic molecules may not only be conserved from the stool product throughout the process described herein, but their concentrations are slightly increased after the sterilization process step of autoclaving. Valerate may also be an important short chain fatty acid and is maintained at an estimated concentration of 38 µg/g in the sterilized lyophilized FSP product compared to concentrations of 18-45 µg/g valerate obtained using a traditional FMT procedure.

Still referring to FIG. 1, another class of biological macromolecules present in postbiotics may be bile acids. There is evidence that several secondary bile acids, including the ones identified using metabolomics analysis in the composition, act as immunomodulators that can induce T regulatory cells instead of Th17. The secondary bile acid, ursodeoxycholic acid (UDCA), has long been used in the treatment of liver disease. Several synthetic bile acids may be pipeline blockbuster drugs for NASH and NAFLD. Taurodeoxycholic acid (TDCA) is another secondary bile acid that has may impact immune function. The sterilization and lyophilization method disclosed herein maintain the composition of secondary bile acids and reveal a significantly increased concentration of taurodeoxycholate specifically.

Still referring to FIG. 1, another biological macromolecule that may be present in the sterilized FSP products are amino acid derivatives or tryptophan metabolites. Tryptophan metabolites have been studied for their role in neuro-immunomodulation and inflammatory signaling. Indole derivatives may bind the aryl hydrocarbon receptor which has a broad array of functions including impacting immune activation. Indole-3-propionic acid contributes to remission through an IL-10 mediated immune pathway in human and mouse models of colitis. This class of molecules is conserved in the sterilization method described herein.

Still referring to FIG. 1, composition 100 further includes a plurality of agents 124. In this disclosure, "agent" refers to a chemical compound substance that exerts a force or effect for a specific purpose. In other words, a plurality of agents 124 are a plurality of substances capable of producing a specific effect. For example, but without limitation, skin irritation may be a resultant of skin contact with some sort of degreasing agents. Moreover, plurality of agents 124 may include a screening agent. Plurality of agents 124 may also include a vitamin. Plurality of agents 124 may also include an essential oil. Plurality of agents 124 may further include a plant protein. Plurality of agents 124 may also include an anti-oxidizing agent. Plurality of agents 124 may also include a preserving agent. Plurality of agents 124 may include a fragrance. Plurality of agents 124 may also include a ceramide. Plurality of agents 124 may further include a moisturizing agent. Plurality of agents 124 may include a lubricating agent. Plurality of agents 124 may also include a polysaccharide. Plurality of agents 124 may also include a filler. Other types of agents may include, without limitation, dust, pollen, cement, asbestos, benzene, or the like. Plurality of agents 124 may be any chemical substance that impacts another. In some embodiments, agent 124 of composition 100 may vary depending on the desired effect. As a non-limiting example, composition 100 may include cinnamon, American *ginseng*, probiotics, berberine, gymnemate, vitamin D, or the like of agent 124 to regulate blood glucose level. As another non-limiting example, composition 100 may include β-blockers, Antiarrhythmic drugs, low-dose muscarinic receptor blockers, or the like of agent 124 to regulate heart rate variability. In some embodiments, composition 100 may include alproic acid, CHIR-99021, E-616452, tranylcypromine, forskolin, CHIR-99021, E-616452, TTNPB, Y-27632, smoothened agonist, and ABT-869, or the like. Further examples of agent 124 are described in this disclosure.

Still referring to FIG. 1, plurality of agents 124 may include at least a co-emulsifying agent. A "co-emulsifying agent," as used in this disclosure, is a type of chemical compound that permits the mixing of two or more liquids. At least a co-emulsifying agent may also keep the mixture together and prevent the two or more liquids from separating. At least a co-emulsifying agent may be referred to as a "co-emulsifier" and helps mix compounds in composition 100. As an example, without limitation, at least a co-emulsifying agent may help mix oil and water together and keep it together as a mixture without separation. At least a co-emulsifying agent may include cetyl alcohol. At least a co-emulsifying agent may also include stearyl alcohol. At least a co-emulsifying agent may include octacosanol. At least a co-emulsifying agent may further include palmitic acid. At least a co-emulsifying agent may include stearic acid. Additionally, at least a co-emulsifying agent may also include surfactants, which are agents that work by lowering the surface tension of different liquids. At least a co-emulsifying agent may also include monoglycerides, diglycerides, polyoxethylene derivatives, egg yolk, diacetyl tartaric acid esters of monoglycerides (DATEM), polyglycerol ester (PGE), sorbitan ester (SOE) and PG ester (PGME).

Still referring to FIG. 1, composition 100 includes a plurality of agents 124 configured to regulate biomarkers of aging. For the purposes of this disclosure, a "biomarker" is a measurable biological characteristic or molecule. A "biomarker of aging," as used in this disclosure, is any biological indicator used to measure and/or assess the quality of aging in a living organism. Biomarker may include molecular, histologic, radiographic, or physiologic characteristics of a living organism. As a non-limiting example, biomarker of aging or baseline biomarker of aging measurement may be obtained using MRI, PET, or CT scans. As another non-limiting example, biomarker of aging or baseline biomarker of aging measurement may be obtained using mRNA sequencing as described in this disclosure. As another non-limiting example, biomarker of aging or baseline biomarker of aging measurement may be obtained using physical examination measuring vital signs like blood pressure, heart rate, respiratory rate, body temperature, or the like. Biomarker may include any qualitative and/or quantitative measurement. For example, and without limitation, biomarker of aging may include levels and quality of glucose, insulin, triglycerides, AMPK, mTOR activity, growth factors, glial cells, neurons, blood, vitamins, enzyme, cholesterol, hormones, and gut bacteria. In some embodiments, composition 100 may be used to treat and/or reverse age-related disease (ARD) and effects of aging. Additionally, composition 100 may have an effect on a baseline biomarker of aging measurement, alone or in combination with a plurality of biological indicators. For the purposes of this disclosure, a "baseline biomarker of aging measurement" is the initial measurement or starting point of a specific biomarker associated with aging. In some embodiments, baseline biomarker of aging measurement may include biomarker of aging as described further in this disclosure. In some embodiments, baseline biomarker of aging measurement may include baseline biomarker of neurodegeneration as described in this disclosure. For the purposes of this disclosure, "baseline biomarker of neurodegeneration" is a measurable characteristic or molecule that is indicative of the initial or starting point of neurodegenerative processes.

In some embodiments, a plurality of baseline biomarkers of aging measurement may be used to monitor and track the impact of composition 100 in a subject. For the purposes of this disclosure, a "subject" is any organism that receives a composition. As a non-limiting example, subject may include humans, mice, Caenorhabditis elegans (C. elegans), or the like. In some embodiments, subject may include a plurality of subjects. As a non-limiting example, composition 100 may be administered to a plurality of subjects using a plurality of dose schedules 128.

With continued reference to FIG. 1, in some embodiments, biomarker of aging may include genes. As a non-limiting example, biomarker of aging may include kgb-1, fat-5, ftt-2, or the like. As another non-limiting example, biomarker of aging may include Kyn, NT-BNP, cTNI, or the like. As another non-limiting example, biomarker of aging may include a sod-2 gene. For the purposes of this disclosure, "sod-2," also called as "manganese superoxide dismutase" is the ROS detoxifying enzyme of cells. The sod-2 gene plays a crucial role in the human body by encoding the enzyme responsible for neutralizing harmful superoxide radicals and protecting cells against oxidative stress in the mitochondria. Superoxide radicals are natural byproducts of cellular metabolism and can cause damage to DNA, proteins, and lipids through oxidative stress. The sod-2 enzyme converts superoxide radicals into less reactive forms, which can then be further broken down into water and molecular oxygen. By efficiently scavenging superoxide radicals and preventing their accumulation, sod-2 helps maintain the delicate balance between oxidative stress and antioxidant defense within cells. The sod-2 gene is located in the mitochondrial matrix, where it shields these organelles from oxidative damage. Composition 100 may reduce reduced sod-2 expression. As a non-limiting example, when 0.05 mg/mL of composition 100 is administered to C. elegans and analyzed by mRNA sequencing, reduced sod-2 expression may be observed on day 9 of the observation but had no change may be observed on day 2 of the observation (i.e. −0.372 fold-change, p-value <0.1). In a non-limiting example, this may be resulted as low-level ROS signaling is inhibited by the potent anti-oxidant capacity of composition 100. As Low-level ROS signaling regulates many biological processes related to aging, the down-regulation of sod-2 may adjust ROS production in a way that optimizes this beneficial signaling process. In another non-limiting example, this may be resulted as downregulating the expression of sod-2 induces a hormetic response from the slight increase in oxidative stress within the mitochondria. This can result in a mild stress response triggering other cellular antioxidant mechanisms to compensate and ultimately enhancing overall antioxidant capacity, cellular repair, and proteostasis. This may effectively increase stress resistance and potentially extend lifespan (i.e. anti-aging).

With continued reference to FIG. 1, as another non-limiting example, biomarker of aging may include a hif-1α gene. For the purposes of this disclosure, a "hif-1α," also called "Hypoxia-inducible factor 1-alpha" is a subunit of a heterodimeric transcription factor hypoxia-inducible factor 1. hif-1α serves a vital function in the human body by regulating the response to low oxygen levels, known as hypoxia. hif-1α acts as a transcription factor that orchestrates adaptive cellular responses to oxygen deprivation. When oxygen levels are reduced, hif-1α is stabilized and translocated to the nucleus, forming a complex with hif-1β. This complex binds to specific DNA sequences, called hypoxia response elements (HREs), and activates the expression of genes involved in multiple physiological processes. hif-1α promotes angiogenesis, the formation of new blood vessels, to enhance oxygen and nutrient supply to oxygen-deprived tissues. Additionally, hif-1α induces the production of erythropoietin (EPO), a hormone that stimulates the generation of red blood cells, boosting oxygen-carrying capacity. hif-1α also regulates metabolic adaptation by promoting glycolysis, the breakdown of glucose, and inhibiting mitochondrial respiration and thereby reducing mitochondrial oxidative stress. Moreover, hif-1α influences the immune response, inflammation, and tissue repair processes. In some embodiments, when 0.05 mg/mL of composition 100 is administered to C. elegans and analyzed by mRNA sequencing, increased hif-1α expression may be observed on day 2 of observation but no change may be observed in expression on of observation (i.e. 0.268 fold-change, p-value <0.1). In a non-limiting example, this may be resulted as the upregulation of Hif-1α early in the lifespan may increase angiogenesis enhancing tissue oxygenation and nutrient supply, and potentially may improve cellular function and survival. Further, the hif-1α-induced shift towards glycolysis may reduce mitochondrial oxidative stress. In another non-limiting example, this may be resulted as the upregulation of hif1a at Day 2 activated autophagy, a process where cells recycle damaged intracellular components to maintain homeostasis. hif-1α 's link to autophagy and lifespan extension is documented.

With continued reference to FIG. 1, as another non-limiting example, biomarker of aging may include a gst-7 gene. For the purposes of this disclosure, a "gst-7 gene," also called "probable glutathione S-transferase 7" is the conjugation of reduced glutathione to exogenous and endogenous hydrophobic electrophiles. The GST-7 gene encodes a glutathione S-transferase (GST) enzyme. gst enzymes conjugate reduced glutathione (GSH) to various exogenous and endogenous electrophiles. This conjugation reaction detoxifies these electrophiles, making them less harmful to the cell. The gst-7 gene is expressed in various tissues, including the liver, kidney, and brain. The gst-7 gene can detoxify environmental pollutants, such as herbicides and pesticides. The gst-7 gene can detoxify endogenous compounds, such as ROS produced by the mitochondria. gst-7 may affect neurological function and aging. In some embodiments, gst-7 may develop Alzheimer's disease-like symptoms. As a non-limiting example, gst-7 may protect neurons from damage. As another non-limiting example, gst-7 may decrease with increasing age and This may contribute to age-related declines in cognitive function. In some embodiments, when 0.05 mg/mL of composition 100 is administered to C. elegans and analyzed by mRNA sequencing, decreased gst-7 expression may be observed on day 9 of observation but had no change in expression may be observed on day 2 (i.e. −0.322 fold-change, p-value <0.1). In a non-limiting example, this may be resulted as the downregulation of gst-7 induces a hormetic response by slightly increasing oxidative stress that triggers an adaptive response that promotes other antioxidant defenses, improves protein homeostasis, and enhances DNA repair mechanisms. In another non-limiting example, this may be resulted as gst-7 has a role in the cellular signaling cascade of apoptosis (programmed cell death), by reducing gst-7 expression at day 9 of observation, composition 100 may promote cellular survival, growth, and differentiation.

With continued reference to FIG. 1, as another non-limiting example, biomarker of aging may include a FOXA1 gene. The FOXA1 gene (pha-4 in C. elegans) codes for the transcription factor, FOXA1. FOXA1 is critical in various cellular processes, including oxidative stress, mitochondrial function, and neurological function. For the purposes of this disclosure, a mitochondrial function" is the biological processes and activities that occur within mitochondria. As a non-limiting example, mitochondrial function may include ATP production, metabolic pathways, calcium regulation, ROS management, apoptosis regulation, or the like. In terms of oxidative stress, FOXA1 may protect cells from damage caused by free radicals by activating genes that produce antioxidants. FOXA1 may regulate mitochondrial function by activating genes that are involved in the production of ATP. In terms of neurological function, FOXA1 is expressed in a number of brain regions, including the hippocampus, which is involved in learning and memory. FOXA1 may regulate the expression of genes that are involved in the formation of new synapses between neurons. Finally, FOXA1 expression decreases with age, and this may contribute to the age-related decline in cognitive function. FOXA1 may regulate the expression of genes that are involved in the repair of DNA damage, and this may help to protect cells from damage that can lead to cancer or cell death. In some embodiments, when 0.05 mg/mL of composition 100 is administered to *C. elegans* and analyzed by mRNA sequencing, increased pha-4 expression may be observed on day 2 of observation but had no change in expression may be observed on day 9 of observation (i.e. 0.495 fold-change, p-value <0.1). In a non-limiting example, this may be resulted as the increased expression of FOXA1 (PHA-4) improves the metabolic efficiency, DNA repair, and production of antioxidants leading to an increase in lifespan.

With continued reference to FIG. 1, in some embodiments, biomarkers may include telomere length, C-reactive protein, small dense low-density lipoprotein particles, homocysteine, Hemoglobin A1C, vitamin D, fasting insulin, immune cells, such as, but not limited to T cells, B cells, natural killer (NK) cells, and the like, epigenetic markers, proteomics, metabolomics, genome sequencing, and any other biomarker for aging described throughout this disclosure further below. In a non-limiting example, T cells may include T-regulatory cell, naïve T cell, or the like. For the purposes of this disclosure, an "epigenetic marker" is chemical modifications on DNA or histone proteins that can influence gene expression without altering the underlying DNA sequence. As a non-limiting example, epigenetic marker may include DNA methylation (i.e. methylation marker), histone modification, such as, but not limited to, acetylation, methylation, phosphorylation, ubiquitination, or the like. For the purposes of this disclosure, "methylation marker" is a specific site on the DNA molecule where a methyl group is added to a cytosine base. In DNA methylation, a methyl group is added to the cytosine base of DNA at specific regions called CpG sites (Cytosine-phosphate-Guanine). CpG sites are regions in the DNA where a cytosine is followed by a guanine nucleotide. Methylation at CpG sites can regulate gene expression by either promoting or inhibiting the binding of transcription factors and other regulatory proteins to the DNA. In a non-limiting example, the epigenetic marker and the methylation marker may be analyzed to obtain baseline biomarker of aging measurement. In another non-limiting example, the change the epigenetic marker and the methylation marker may be analyzed to find the efficacy of composition 100 (i.e. the change in baseline biomarker of aging measurement). The DNA methylation disclosed herein is further described below. In some embodiments, composition 100 may be used to decrease mTOR activity. "mTOR," as used in this disclosure, is a key initiator of the senescence-associated secretory phenotype (SASP). Interleukin 1 alpha (IL1A) may be found on the surface of senescent cells where it contributes to the production of SASP factors due to a positive feedback loop with NF-κB. Translation of mRNA for IL1A may be highly dependent upon mTOR activity. mTOR activity may increase levels of IL1A, mediated by MAPKAPK2. mTOR inhibition of ZFP36L1 prevents this protein from degrading transcripts of numerous components of SASP factors. Decreased mTOR activity may increase life span in *S. cerevisiae, C. elegans*, and *D. melanogaster*. For example, composition 100 may include a mTOR inhibitor such as rapamycin and rapalogs. mTOR inhibitors are a class of drugs that inhibit the mechanistic target of rapamycin (mTOR), which is a serine/threonine-specific protein kinase that belongs to the family of phosphatidylinositol-3 kinase (PI3K) related kinases (PIKKs). mTOR inhibitors may be useful for treating/preventing several age-associated conditions, including neurodegenerative diseases such as Alzheimer's disease and Parkinson's disease. Rapamycin and rapalogs may be a macrolide compound that is used to coat coronary stents, prevent organ transplant rejection, treat a rare lung disease called lymphangioleiomyomatosis, and treat perivascular epithelioid cell tumor (PEComa). It may have immunosuppressant functions in humans and is especially useful in preventing the rejection of kidney transplants. It may be a mechanistic target of rapamycin kinase (mTOR) inhibitor that inhibits activation of T cells and B cells by reducing their sensitivity to interleukin-2 (IL-2). Rapamycin may inhibit mTORC1 so that the phosphorylation of GS (glycogen synthase) can be increased in skeletal muscle. This discovery represents a potential novel therapeutic approach for glycogen storage disease that involve glycogen accumulation in muscle. Composition 100 may include first generation mTOR inhibitors such as temsirolimus (CCI-779), everolimus (RAD001), and ridaforolimus (AP-23573), Umirolimus, Zotarolimus. Composition 100 may include second generation mTOR inhibitors such as ATP-competitive mTOR kinase inhibitors. For example, torin-1, torin-2 and vistusertib. Temsirolimus and everolimus may be used in the treatment of a variety of malignancies, including renal cell carcinoma (temsirolimus) and pancreatic cancer, breast cancer, and renal cell carcinoma (everolimus). Additionally, composition 100 may include various natural compounds, including epigallocatechin gallate (EGCG), caffeine, curcumin, berberine, quercetin, resveratrol and pterostilbene, may inhibit help to mTOR.

Still referring to FIG. 1, composition 100 may include a plurality of agents 124 to increase insulin-like growth factor 1 (IGF-1) levels. "IGF-1," as used in this disclosure, is a hormone similar in molecular structure to insulin which plays an important role in childhood growth and has anabolic effects in adults. As a major growth factor, IGF-1 may be responsible for stimulating growth of all cell types and causing significant metabolic effects. One important metabolic effect of IGF-1 may be its ability to signal cells that sufficient nutrients are available for cells to undergo hypertrophy and cell division. These signals may also enable IGF-1 to inhibit cell apoptosis and increase the production of cellular proteins. IGF-1 is a primary mediator of the effects of growth hormone (GH). Growth hormone is made in the anterior pituitary gland, is released into the blood stream, and then stimulates the liver to produce IGF-1. IGF-1 then stimulates systemic body growth and has growth-promoting effects on almost every cell in the body, especially skeletal muscle, cartilage, bone, liver, kidney, nerve, skin, hematopoietic, and lung cells. In addition to the insulin-like effects, IGF-1 can also regulate cellular DNA synthesis. IGF-1 plays an important role in growth and continues to have anabolic effects in adults—meaning that it can induce hypertrophy of skeletal muscle and other target tissues. The concentrations of IGF-1 decrease with age and during inflammation. Alzheimer's disease and dementia are associated with lower IGF-1 levels and increasing IGF-1 can help prevent the accumulation of amyloid plaque in the brain. Other neurodegenerative diseases, such as Amyotrophic Lateral Sclerosis (ALS) and Parkinson's disease, are also associated with lower IGF-1 levels, and increasing IGF-1 can help lower your risk of developing these diseases. IGF-1 helps prevent cognitive decline and brain aging by protecting existing brain cells and promoting the growth of new brain cells. IGF-1 improves learning and memory. IGF-1 speeds up executive functions and mental processing. IGF-1 increases brain-derived neurotrophic factor (BDNF). IGF-1 may improve gut health and help reduce gut permeability, which affects brain health. IGF-1 promotes synaptogenesis. IGF-1 stimulates myelin production. IGF-1 supports neurogenesis and neuroplasticity. Composition 100 may include agents 124 to increase and regulate IGF-1 serum of IGF-1 receptor levels, such as, phosphate, zinc, vitamin c, protein, magnesium, selenium, cinnamon, vitamin d, thiamine, probiotics (e.g., *Lactobacillus acidophilus, Lactobacillus casei, Lactobacillus rhamnosus, Bifidobacterium longum*), dehydroepiandrosterone, taurine, resveratrol, leucine, astragalus, colostrum, Acetyl-L-Carnitine, creatine, ursolic acid, hydroxy methyl butyrate, coenzyme Q10, and similar agents.

Still referring to FIG. 1, composition 100 may include a plurality of agents 124 to activate 5' AMP-activated protein kinase (AMPK). "AMPK," as used in this disclosure, is an enzyme that plays a role in cellular energy homeostasis, largely to activate glucose and fatty acid uptake and oxidation when cellular energy is low. It is expressed in a number of tissues, including the liver, brain, and skeletal muscle. The net effect of AMPK activation is stimulation of hepatic fatty acid oxidation, ketogenesis, stimulation of skeletal muscle fatty acid oxidation and glucose uptake, inhibition of cholesterol synthesis, tumor suppression, lipogenesis, and triglyceride synthesis, inhibition of adipocyte lipogenesis, inhibition of adipocyte lipolysis, and modulation of insulin secretion by pancreatic β-cells. Composition 100 may include activating agents such as biguanides, thiazolidinediones, polyphenols, ginsenoside, α-Lipoic acid, and other AMPK modulators.

Still referring to FIG. 1, composition 100 may include a plurality of agents 124 configured to regulate heart rate variability. "Heart rate variability (HRV)," as used in this disclosure, is the physiological phenomenon of variation in the time interval between heartbeats. It is measured by the variation in the beat-to-beat interval. A reduction of HRV has been reported in several cardiovascular and non-cardiovascular diseases. Depressed HRV after Myocardial infarction (MI) may reflect a decrease in vagal activity directed to the heart. HRV in patients surviving an acute MI reveal a reduction in total and in the individual power of spectral components. In neuropathy associated with diabetes mellitus characterized by alteration in small nerve fibers, a reduction in time domain parameters of HRV seems not only to carry negative prognostic value but also to precede the clinical expression of autonomic neuropathy. A reduced HRV may be observed consistently in patients with cardiac failure. Liver cirrhosis is associated with decreased HRV. Decreased HRV in patients with cirrhosis has a prognostic value and predicts mortality. Loss of HRV may be also associated with higher plasma pro-inflammatory cytokine levels and impaired neurocognitive function in this patient population. HRV may be decreased in patients with sepsis. Loss of HRV has both diagnostic and prognostic value in neonates with sepsis. Interventions that augment HRV may be protective against cardiac mortality and sudden cardiac death. In light of this, agent 124 of composition 100 may include β-blockers, antiarrhythmic drugs, low-dose muscarinic receptor blockers, and similar agents to regulate HRV. For the purposes of this disclosure, "β-blockers" are a class of medications that block the beta-adrenergic receptors in the heart. By doing so, β-blockers can reduce the effects of sympathetic activity, specifically the binding of adrenaline and noradrenaline to these receptors. This results in a decrease in sympathetic tone and a subsequent increase in parasympathetic activity, leading to an overall increase in HRV. For the purposes of this disclosure, "antiarrhythmic drugs" are medications used to treat abnormal heart rhythms. Some antiarrhythmic drugs, such as those belonging to class III (e.g., amiodarone, sotalol), can modulate HRV by affecting the electrical activity and repolarization of cardiac cells. Muscarinic receptor blockers, also known as anticholinergic drugs, work by blocking the action of acetylcholine at muscarinic receptors. By blocking the parasympathetic (cholinergic) influence on the heart, these agents 124 can increase sympathetic activity and decrease HRV. In a non-limiting example, composition 100 may be configured to regulate cardiac remodeling, heart failure, or the like.

Still referring to FIG. 1, composition 100 may include a plurality of agents 124 to regulate blood glucose levels. Glucose is one of the body's principal fuels. It is an energy-rich monosaccharide sugar that is broken down in our cells to produce adenosine triphosphate (ATP). ATP is a small packet of chemical energy that powers the millions of biochemical reactions that take place in the body every second. As the human body ages, muscle and other tissues become less sensitive to insulin. This means that sugar (glucose) and fat (triglycerides) remain in the bloodstream longer, leading to poor blood sugar and blood lipid control. Age related diseases correlated to irregular blood glucose levels includes diabetes. Diabetes is a disease that affects many older adults. People may get diabetes when their blood glucose, also called blood sugar, is too high. Additionally, blood glucose monitoring may include continuous blood glucose monitoring biomarkers such as a comprehensive metabolic panel (CMP), complete blood count (CBC), lipid panel, and similar blood tests. Composition 100 may include agents 124 such as cinnamon, American *ginseng*, probiotics, aloe vera, berberine, vitamin d, gymnemate, and similar agents to regulate blood glucose levels. As a non-limiting example, cinnamon can enhance insulin sensitivity, improve glucose metabolism, and lower blood glucose levels. Some compounds found in cinnamon, such as cinnamaldehyde, may act by mimicking insulin or enhancing insulin signaling. As another non-limiting example, American *ginseng* may include a hypoglycemic effect by improving insulin sensitivity or increasing glucose uptake by cells. It may also influence glucose metabolism and reduce postprandial (after-meal) blood glucose spikes. As another non-limiting example, probiotics may affect the gut microbiota composition, which can influence various metabolic processes, including glucose homeostasis. As another non-limiting example, aloe vera may enhance insulin sensitivity, stimulate glucose uptake by cells, or have direct effects on pancreatic beta cells involved in insulin production. As another non-limiting example, berberine may enhance insulin sensitivity, activate enzymes involved in glucose metabolism, and influence cellular signaling pathways related to glucose regulation. As another non-limiting example, gymnemate may affect taste perception, reduce sugar cravings, and potentially influence insulin secretion.

Still referring to FIG. 1, composition 100 may include a plurality of agents 124 related to neurotherapeutics. "Neurotherapeutics," as used in this disclosure, are substances used in the prevention and treatment of neurological diseases and disorders. Neurological diseases and disorders may include Neuropathy—this nerve disorder causes symptoms such as numbness and weakness, often affecting the hands and feet. It can be the result of systemic diseases such as diabetes, as well as medications and other causes; Alzheimer's disease; Parkinson's disease—a chronic and progressive movement disorder, Parkinson's disease involves the malfunction and death of vital nerve cells in the brain. Treatment options include medication and surgery to manage symptoms; Myopathy—a disorder of the muscles, myopathy is characterized by muscle weakness that is usually the most severe in the upper arms and thighs; Amyotrophic Lateral Sclerosis—also known as ALS or Lou Gehrig's disease, this is a progressive disease affecting motor neurons and causes deterioration of the body's muscle function. Stroke—this dangerous, life-threatening event occurs when the blood supply to a part of the brain is suddenly interrupted or when a blood vessel in the brain bursts; Myasthenia Gravis—a chronic autoimmune disorder, this disease blocks the signals from the nerves to the muscles and makes the muscles unable to move. A key indication of the disease is muscle weakness that increases during periods of activity and improves after periods of rest; and Muscular Dystrophy—a group of progressive muscle disorders that has a genetic basis. Symptoms begin with a weakening of the muscles closest to the trunk of the body and later progress to severe muscle deterioration and muscle contraction. In some embodiments, composition 100 may be used to treat and/or reverse neurodegeneration and have an effect on a baseline biomarker of aging measurement, alone or in combination with a plurality of biological indicators. As used in this disclosure, "neurodegeneration," is the progressive atrophy and loss of function of neurons, which is present in neurodegenerative diseases. As a non-limiting example, neurodegenerative disease may include Alzheimer's disease and Parkinson's disease. In some embodiments, a plurality of baseline biomarkers of aging may be used to monitor and track the impact of composition 100 in a subject regarding neurodegeneration. In some embodiments, biomarkers may include Amyloid beta (Aβ), BACE1, Soluble Aβ precursor protein (sAPP), proteins, Autoantibodies, and Cerebrospinal fluid biomarkers (i.e., CSF oligomeric α-synuclein, CSF phosphorylated a-synuclein, CSF α-synuclein aggregates, α-Synuclein species in the blood, Lysosomal enzymes, etc.), and any other biomarker of aging related to neurology described throughout this disclosure further below.

Still referring to FIG. 1, composition 100 may include neurotherapeutic agents such as Acetyl-L-Carnitine, Alpha-Lipoic Acid, B Vitamins, Curcumin, Fish Oil, N-Acetyl Cysteine, and similar agents. Acetyl-L-carnitine is an amino acid and antioxidant that creates healthy nerve cells, reduces nerve pain, and raises energy levels. It has been found to improve cancer-associated fatigue, as well as chemotherapy-induced neuropathy. It may be taken as a supplement or found in foods like meat, fish, poultry, and dairy products. Alpha-lipoic acid is an antioxidant known for its ability to improve nerve function, relieve nerve dysfunction symptoms, and lower blood sugar levels. It may be administered intravenously, through a capsule supplement, or by eating certain foods. These may include broccoli, red meat, liver, Brussels sprouts, spinach, and brewer's yeast. B vitamins are known for their ability to support healthy nervous system function. Vitamins B-1, B-6, and B-12 have been found to be especially beneficial for treating neuropathy. Vitamin B-1, also known as thiamine, may help to reduce pain and inflammation and vitamin B-6 preserves the covering on nerve endings. B-12 is also essential for proper neurological function and a B-12 deficiency can actually cause neuropathy. B vitamins may be supplemented or can be found in eggs, seafood, fortified cereals, vegetables, low-fat dairy products, and poultry. Curcumin is a strong antioxidant found in turmeric known for its anti-inflammatory and analgesic properties. When taken early on, curcumin may prevent chronic pain associated with neuropathy. It may also reduce pain and inflammation. It may be taken as a supplement or used as an herbal add-on to certain foods. Fish oil may work as an anti-inflammatory and can repair nerve damage. Research has shown that fish oil may slow the progression of neuropathy and can even reverse it in some cases. It also may promote neuron outgrowth. Fish oil may be taken as a supplement or it can be found in salmon, sardines, mackerel, cod liver oil, herring, oysters, anchovies, or caviar. The omega-3 fatty acids found in fish oil can also be found in walnuts, canola oil, chia seeds, flaxseeds, and soybeans. N-Acetyl-Cysteine is an antioxidant and amino acid that is used to treat nerve pain and reduce inflammation. It may reduce neuropathic pain, improve motor coordination, and improve nerve damage. Since it is not naturally found in foods, it may be taken as a supplement.

Still referring to FIG. 1 composition 100 may contain neurotherapeutics to improve the function of glial cells. "Glia," also called glial cells (singular gliocyte) or neuroglia, as used in this disclosure, are non-neuronal cells in the central nervous system (brain and spinal cord) and the peripheral nervous system that do not produce electrical impulses. They may maintain homeostasis, form myelin in the peripheral nervous system, and provide support and protection for neurons. In the central nervous system, glial cells may include oligodendrocytes, astrocytes, ependymal cells, and microglia, and in the peripheral nervous system glial cells include Schwann cells and satellite cells. They may have four main functions: (1) to surround neurons and hold them in place; (2) to supply nutrients and oxygen to neurons; (3) to insulate one neuron from another; (4) to destroy pathogens and remove dead neurons. They may also play a role in neurotransmission and synaptic connections, and in physiological processes like breathing. Additionally, they may affect both the preservation and consolidation of memories. Composition 100 may include agents to increase the quantity and/or improve the quality of glial cells, for example, fibroblast growth factor-2 (FGF2), glial cell line-derived neurotrophic factor (GDNF), cerebral dopamine neurotrophic factor (CDNF), mesencephalic astrocyte derived neurotrophic factor (MANF), brain-derived neurotrophic factor (BDNF), epidermal growth factor (EGF) and heparin-binding epidermal growth factor (HB-EGF). Growth factors such as these may increase the number of glial cells and block the decrease caused by chronic stress exposure by promoting the generation of new glial cells.

Referring still to FIG. 1, composition 100 includes a plurality of dose schedules 128. As used in this disclosure, a "dose schedule," is the amount of a composition to be used for a subject at a given time. In some embodiments, dosage schedule 128 may include a dosage form, including for example a solid or liquid form. As a non-limiting example, composition 100 may be in the form of a solid, such as a pill, a capsule, a tablet, a paste, or a powder. As another non-limiting example, composition 100 may be in the form of a liquid, such as an aerosol, a gel, a lotion, a liquid, a body wash, or the like. In any form, in a non-limiting example, composition 100 may be consumed, ingested, injected, inhaled, inserted and/or applied topically by the subject to enact the benefits of composition 100. In some embodiments, dosage schedule 128 may include frequency, timing, duration, dosage, or the like. As a non-limiting example, dose schedule 128 may include the time when the administration of composition 100 are to be given, the time between the administrations of composition 100, the length of time composition 100 are to be given, and/or the amount of composition 100 to be given at each specific time, respectively. In some embodiments, dosage of composition 100 may range from 50-1,000 milligrams. As a non-limiting example, dosage may include 0.05, 0.25, 1.25 mg/mL, or the like of composition 100. In an embodiment, composition 100 may be given with food. In an embodiment, composition 100 may be given without food. In some embodiments, a dose schedule 128 of composition 100 may be generated based upon the baseline biomarkers of aging measurement to be administered to a subject. In some embodiments, a dose schedule 128 of composition 100 may be generated based upon the baseline biomarkers of neurodegeneration to be administered to a subject. As a non-limiting example, when a dose schedule 128 of 1.25 mg/mL of composition 100 analyzed to reduce oxidative stress effectively compared to 0.05 mg/mL of composition 100, then 0.25 mg/mL of composition 100 may be selected to be administered to a subject, wherein the subject includes a baseline biomarker of aging measurement that indicates that oxidative stress is abnormal. As another non-limiting example, when a dose schedule 128 of 0.05 mg/mL of composition 100 analyzed to regulate blood glucose level effectively compared to 0.25 mg/mL of composition 100, then 0.05 mg/mL of composition 100 may be selected to be administered to a subject, wherein the subject includes a baseline biomarker of aging measurement that indicates that blood glucose level is abnormal.

Still referring to FIG. 1, in some embodiments, composition 100 may be configured to change baseline biomarkers of aging measurement. As a non-limiting example, the change in baseline biomarker of aging measurement may include upregulation of biomarker of aging. For the purposes of this disclosure, an "upregulation" is an increase in the expression, production, or activity of a specific gene, protein, or receptor in a biological system. In a non-limiting example, administering composition 100 to a subject may result in upregulated pud-3, fbxb-88, dao-2, noah-2, let-4, mlt-11, zip-7, Y65B4B M.3, cyp-34A 2, cyp-35B 1, hch-1, noah-1, C09F9.2, dhs-26, plx-2, tbx-8, 1pr-3, cutl-25, dpy-14, sym-1 gene, or the like at day 2 of observation. In another non-limiting example, administering composition 100 to a subject may result in upregulated clx-1, Y6E2A.4, gba-4, F23D12.2, mlt-11, C09F9.2, T28F4.4, sqv-6, R09A8.2, H06H21.37, fbn-1, aagr-1, lact-2, noah-2, ulp-4, F55F10.1, rbm-12, chd-1, F54B3.1, rpc-1 gene, or the like at day 9 of observation. In another non-limiting example, administering composition 100 to a subject may result in upregulated PHA-4, let-363, hif-1, or the like. Additionally, and/or alternatively, the change in baseline biomarker of aging measurement may include upregulation of any biomarker described in this disclosure.

Still referring to FIG. 1, as another non-limiting example, the change in baseline biomarker of aging measurement may include downregulation of biomarker of aging. For the purposes of this disclosure, a "downregulation" is a decrease in the expression, production, or activity of a specific gene, protein, or receptor in a biological system. In a non-limiting example, administering composition 100 to a subject may result in downregulated lips-11, clx-1, clec-9, cnc-6, dod-21, C09B8.4, F14F9.3, B0205.13, ora-1, C40H1.8, F58G6.9, acdh-2, Y48G1BL.5, Y37H2A.14, ugt-19, W09G12.7, sptl-2, K09F6.9, fbxa-197, Y57A10A.5 gene, or the like at day 2 of observation. In another non-limiting example, administering composition 100 to a subject may result in downregulated sri-40, Y54G2A.45, drd-1, F21C10.9, spp-9, irg-4, F55H12.2, nlp-24, K08D8.3, F09G8.5, F18E3.11, nhr-17, F35C11.6, K09C4.5, F26A3.4, irg-5, lbp-8, clec-47, F18E3.13, col-93 gene, or the like at day 9 of observation. In another non-limiting example, administering composition 100 to a subject may result in downregulated sod-2, lgg-1, cpr-1, gst-6, or the like. Additionally, and/or alternatively, the change in baseline biomarker of aging measurement may include downregulation of any biomarker described in this disclosure.

Still referring to FIG. 1, in some embodiments, the change in baseline biomarker of aging measurement may be analyzed as a function of a subject or subject cohort. As a non-limiting example, the change in baseline biomarker of aging measurement may be analyzed as a function of one or more demographic facts about the subject. For example, and without limitation, demographic facts may include a subject's age, gender, smoking, drinking, obesity, stress, exercise, sleep, overall health, and the like. In a non-limiting example, women may have more of immune cells than men, and these differences can be related to things like smoking, drinking, obesity, exercise, and stress.

Still referring to FIG. 1, in some embodiment, the change in baseline biomarker of aging measurement may be analyzed using mRNA sequencing. For the purposes of this disclosure, "mRNA sequencing," also called "RNA-seq" is a technique used to analyze and measure the RNA molecules present in a biological sample. In a non-limiting example, baseline biomarker of aging measurement may be obtained using RNA-seq. RNA-seq can provide insights into the transcriptome, which represents the complete set of RNA molecules expressed by an organism or specific cell type. In a non-limiting example, RNA-seq may include Ribonucleic acid (RNA) extraction, messenger RNA (mRNA) enrichment, complementary DNA (cDNA) library preparation, sequencing, data analysis of the resulting sequence, or the like. As a non-limiting example, mRNA sequencing may include bioinformatic tools, which are software applications, algorithms, or databases specifically designed to analyze, interpret, and manage biological data. In some embodiments, the change in baseline biomarker of aging measurement may be analyzed using bisulfite sequencing, methylation-specific PCR, DNA methylation microarrays, whole-genome bisulfite sequencing, chromatin immunoprecipitation, transcriptomic clock analysis, induced pluripotent stem cell (iPSC) profiler, immunofluorescence, or the like.

Still referring to FIG. 1, in some embodiments, the change in baseline biomarker of aging measurement may be compared with baseline biomarker of aging measurement to generate an efficacy rate of composition 100. For the purposes of this disclosure, an "efficacy rate" is a value representing an evaluation of the change in baseline biomarker of aging measurement. In an embodiment, efficacy rate may be a quantitative characteristic, such as a numerical value within a set range. As another non-limiting example, efficacy rate may include '8' for a score range of 0-10, where '0' represents the minimum efficacy of composition 100 for reversing aging of a subject and '10' represents the maximum efficacy of composition 100 for reversing aging. As another non-limiting example, efficacy rate may include '5' for a score range of −10 to 10, where '−10' represents the minimum efficacy of composition 100 for reversing aging of a subject and '10' represents the maximum efficacy of composition 100 for reversing aging. In other non-limiting embodiments, efficacy rate may be a quality characteristic, such as a color coding, where each color is associated with the efficacy of composition 100. As a non-limiting example, efficacy rate may be red, where red may represent a minimum and/or no efficacy of composition 100 for reversing aging. As another non-limiting example, efficacy rate may be green, where green may represent maximum and/or high efficacy of composition 100 for reversing aging. As another non-limiting example, efficacy rate may be light grey when there is minimum and/or no efficacy of composition 100 and the color may get darker as efficacy of composition 100 increases. In some embodiments, efficacy rate may include low to high scoring. As a non-limiting example, efficacy rate may be low' when there is minimum and/or no efficacy of composition 100 and efficacy rate may be 'high' when there is maximum and/or high efficacy of composition 100. In some embodiments, efficacy rate may be updated in real-time as the change in baseline biomarker of aging measurement changes. As a non-limiting example, when baseline biomarker of aging measurement and a change in baseline biomarker of aging measurement are collected, the value of the baseline biomarker of aging measurement may be subtracted from the value of the baseline biomarker of aging measurement. Continuing the non-limiting example, the resulting value may indicate whether the biomarker increased or decreased and the magnitude of the change, where a positive value may indicate an increase (i.e. upregulation) in the biomarker, while a negative value may indicate a decrease (i.e. downregulation).

Still referring to FIG. 1, in some embodiments, efficacy rate may be generated using an efficacy machine learning model trained with efficacy training data. Efficacy training data may correlate a baseline biomarker of aging measurement data set and a change in baseline biomarker of aging measurement data set to output an efficacy rate. As a non-limiting example, efficacy training data may correlate baseline biomarker of aging measurement of sod-2 and the change in baseline biomarker of aging measurement of down regulation of sod-2 and output correlated efficacy rate. In some embodiments, efficacy training data may be stored in a database. In some embodiments, efficacy training data may be received from one or more users, database, external computing devices, and/or previous iterations of processing. As a non-limiting example, efficacy training data may include instructions from a user, who may be an expert user, a past user in embodiments disclosed herein, or the like, which may be stored in memory and/or stored in database, where the instructions may include labeling of training examples. Efficacy machine learning model and efficacy training data disclosed herein may be consistent with machine learning model and training data described below.

Still referring to FIG. 1, in some embodiments, baseline biomarker of aging measurement may be compared with a chronical age to generate an aging rate of a subject. For the purposes of this disclosure, an "aging rate" is a value representing an evaluation of the biological age of a subject compared to a chronological age of the subject. In an embodiment, aging rate may be a quantitative characteristic, such as a numerical value within a set range. As another non-limiting example, aging rate may include '1.2' for a score range of 0-2.0, where '0' represents the biological age is much higher than the chronical age of a subject, '1.0' represents the biological age and the chronical age is same and '2.0' represents the biological age is much lower than the chronical age of a subject. In other non-limiting embodiments, aging rate may be a quality characteristic, such as a color coding, where each color is associated with the level of difference between the chronological age and biological age of a subject. As a non-limiting example, aging rate may be red, where red may represent the biological age is much higher than the chronical age of a subject. As another non-limiting example, aging rate may be green, where green may represent the biological age is much lower than the chronical age of a subject. As another non-limiting example, aging rate may be light grey when the biological age is much lower than the chronical age of a subject and the color may get darker as the biological age increases higher than the chronical age of a subject. In some embodiments, aging rate may include low to high scoring. As a non-limiting example, aging rate may be low' when the biological age is lower than the chronical age of a subject and aging rate may be 'high' when the biological age is higher than the chronical age of a subject. In some embodiments, aging rate may be updated in real-time as the baseline biomarker of aging measurement or chronological age of a subject changes. As a non-limiting example, the biological age of a subject may be calculated using the baseline biomarker of aging measurement, such as but not limited to DNA methylation patterns, telomere length, or levels of certain proteins in the blood, or the like. For example, and without limitation, the baseline biomarker of aging measurement may be analyzed using an epigenetic clock, or the like. Continuing the non-limiting example, the biological age and the chronological age of a subject may be compared. In a non-limiting example, when the biological age is lower than the chronological age of a subject, then the aging rate may include 'low' or a value higher than '1.0.' In another non-limiting example, when the biological age is higher than the chronological age of a subject, then the aging rate may include 'high' or a value lower than '1.0.' In another non-limiting example, when the biological age equivalent with the chronological age of a subject, then the aging rate may include '1.0.'

Still referring to FIG. 1, in some embodiments, aging rate may be generated using an aging machine learning model trained with aging training data. Aging training data may correlate a baseline biomarker of aging measurement data set and a chronological age data set to output an aging rate. As a non-limiting example, aging training data may correlate baseline biomarker of aging measurement of DNA methylation patterns, telomere length, level of certain proteins in the blood and the chronical age of a subject and output correlated aging rate. In some embodiments, aging training data may be stored in a database. In some embodiments, aging training data may be received from one or more users, database, external computing devices, and/or previous iterations of processing. As a non-limiting example, aging training data may include instructions from a user, who may be an expert user, a past user in embodiments disclosed herein, or the like, which may be stored in memory and/or stored in database, where the instructions may include labeling of training examples. Aging machine learning model and aging training data disclosed herein may be consistent with machine learning model and training data described below.

Figure 2A:
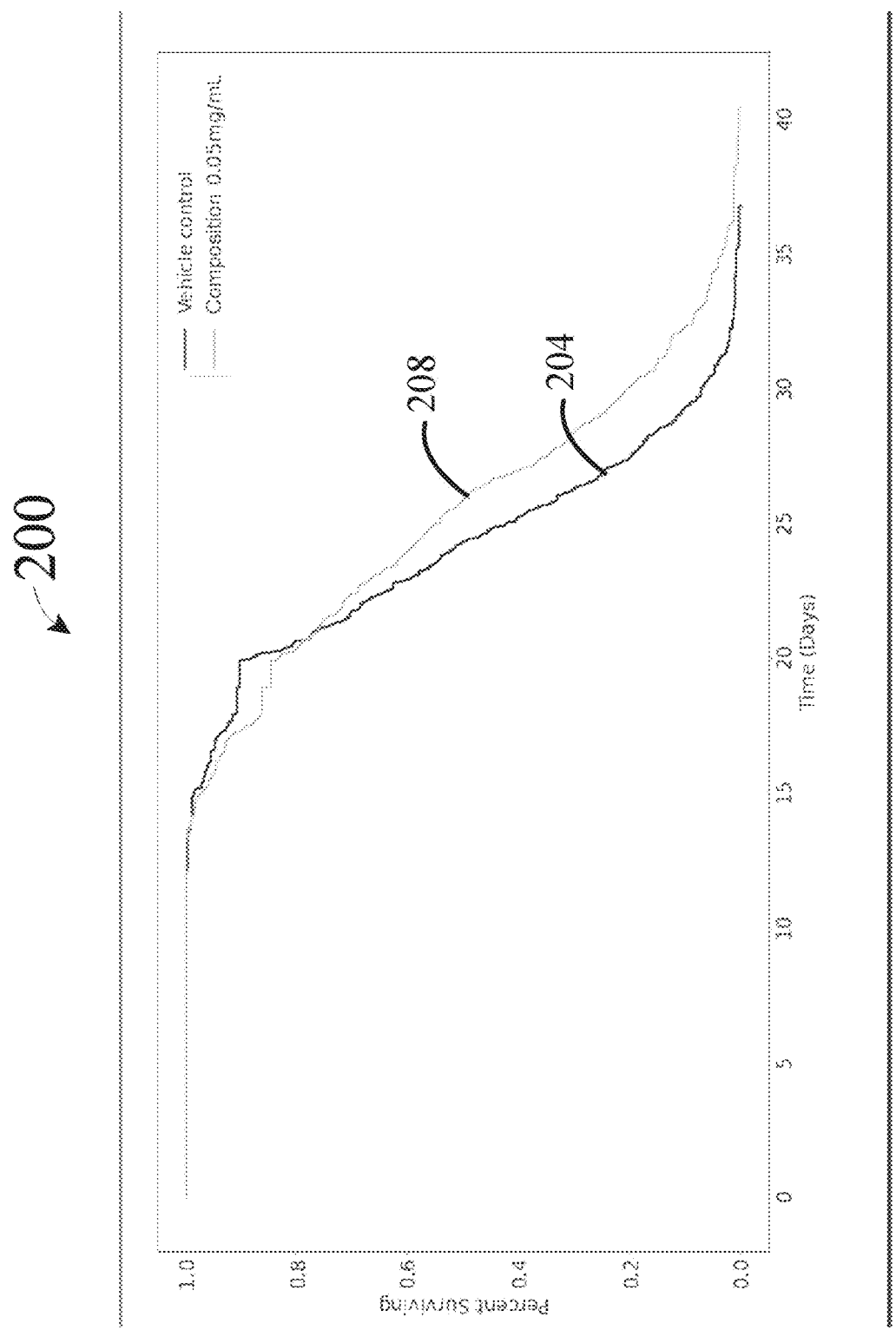
FIG. 2A illustrates a chart illustrating the lifespan effect on *C. elegans* adult animals utilizing the composition.

Referring now to FIG. 2A is a chart 200 illustrating the lifespan effect on *C. elegans* adult animals utilizing composition 100. In this disclosure, *C. elegans* may include a model organism to investigate molecular mechanisms influencing aging, behavior, and toxicity of composition 100. In a embodiments, organisms may include a vehicle control 204. In an embodiment, organisms may be treated with at least 0.05 mg/ml 208 of composition 100 and compared to a "vehicle control," which as used in this disclosure, may include organisms not treated with composition 100. Lifespan data was represented as the percent of organism surviving over time, known as the Kaplan-Meier Estimate of Survival function. Treatments that increased lifespan shifted the curve to the right relative to the vehicle control 204. The survival curve resulting from 0.05 mg/ml 208 of composition 100 treatment is not only right shifted but has a different slope which diverges more from the vehicle control 204 over time after about day 20. This suggests that although there is not a salient early benefit, organisms treated with composition 100 have a relatively lower mortality rate late in life and/or have demonstrated improvement in regard to one or more baseline biomarkers of aging measurement.

Figure 2B:
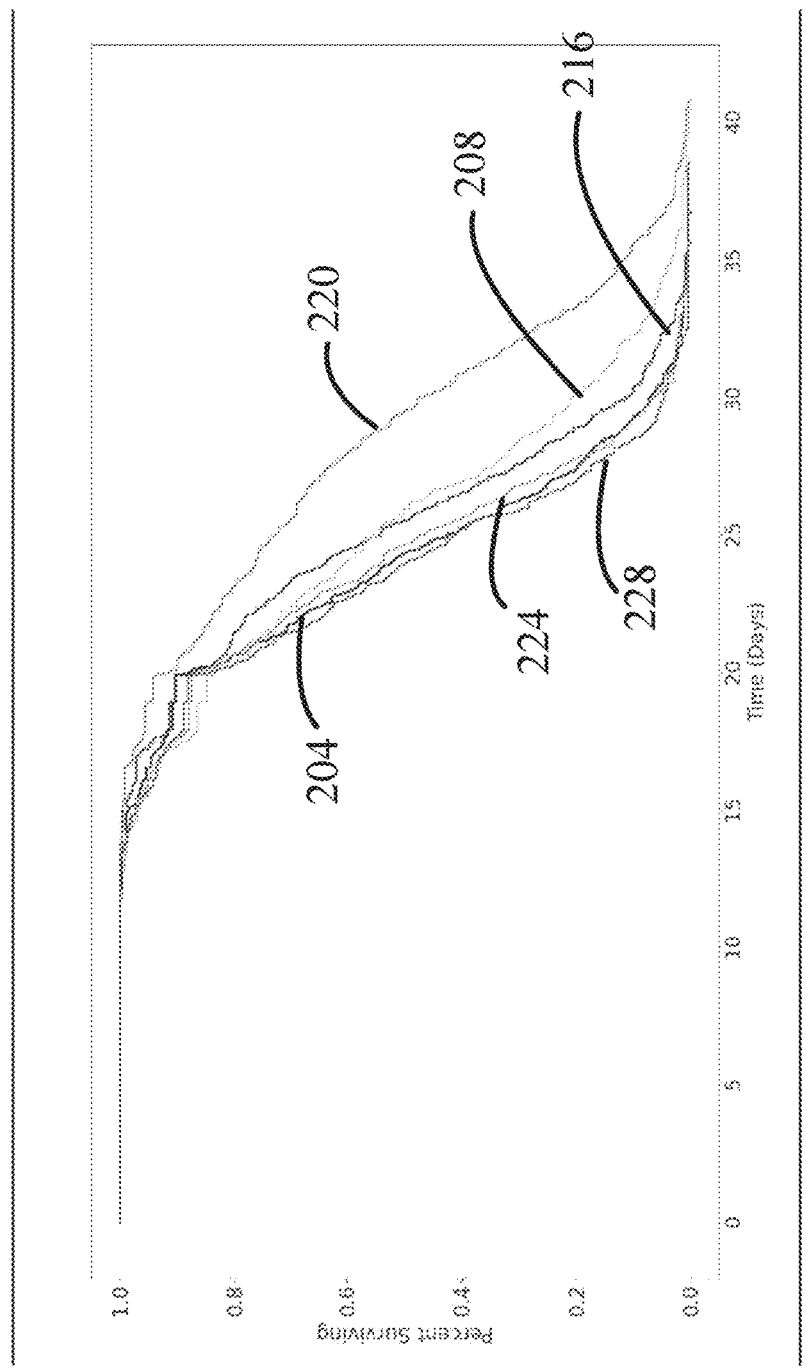
FIG. 2B illustrates a chart illustrating the lifespan effect on *C. elegans* adult animals utilizing the composition.

FIG. 2B is a chart 212 illustrating the lifespan effect on *C. elegans* adult animals utilizing composition 100, following the same study procedures as in FIG. 2A. Chart 212 shows the results of composition 100 varying in mg/ml on the lifespan effect on *C. elegans* adult animals when compared to the vehicle control, resveratrol, and rapamycin. Chart 212 illustrates the impact of resveratrol 216 at 100 μM; and rapamycin 220 at 50 μM; composition 100 at 0.05 mg/ml 208, 0.25 mg/ml 224, and 1.25 mg/ml 228; resveratrol at 100 μM; and rapamycin at 50 μM. In another non-limiting example, subjects, for instance, *C. elegans*, may be divided into five groups, with each group receiving a different concentration of composition (0.05 mg/mL 208, 0.25 mg/mL 224, or 1.25 mg/mL 228), vitamin C as a positive control (10 mM), or dimethyl sulfoxide (DMSO) as a negative control (0.05% DMSO). The results may show that pre-treatment with composition 100 improved oxidative stress tolerance in a dose-dependent manner, with the highest concentration of composition 100 providing the most protection against oxidative stress. The lowest concentration of composition 100 may show greater protection from the oxidative stress induced by the addition of paraquat than the vitamin C positive control group. The positive control group may by an average of 25% over 24 hours post-exposure, while the negative control declined by an average of 41%. In contrast, the group treated with 1.25 mg/mL 228 of composition 100 may decrease by an average of only 3.2%.

Figure 3A:
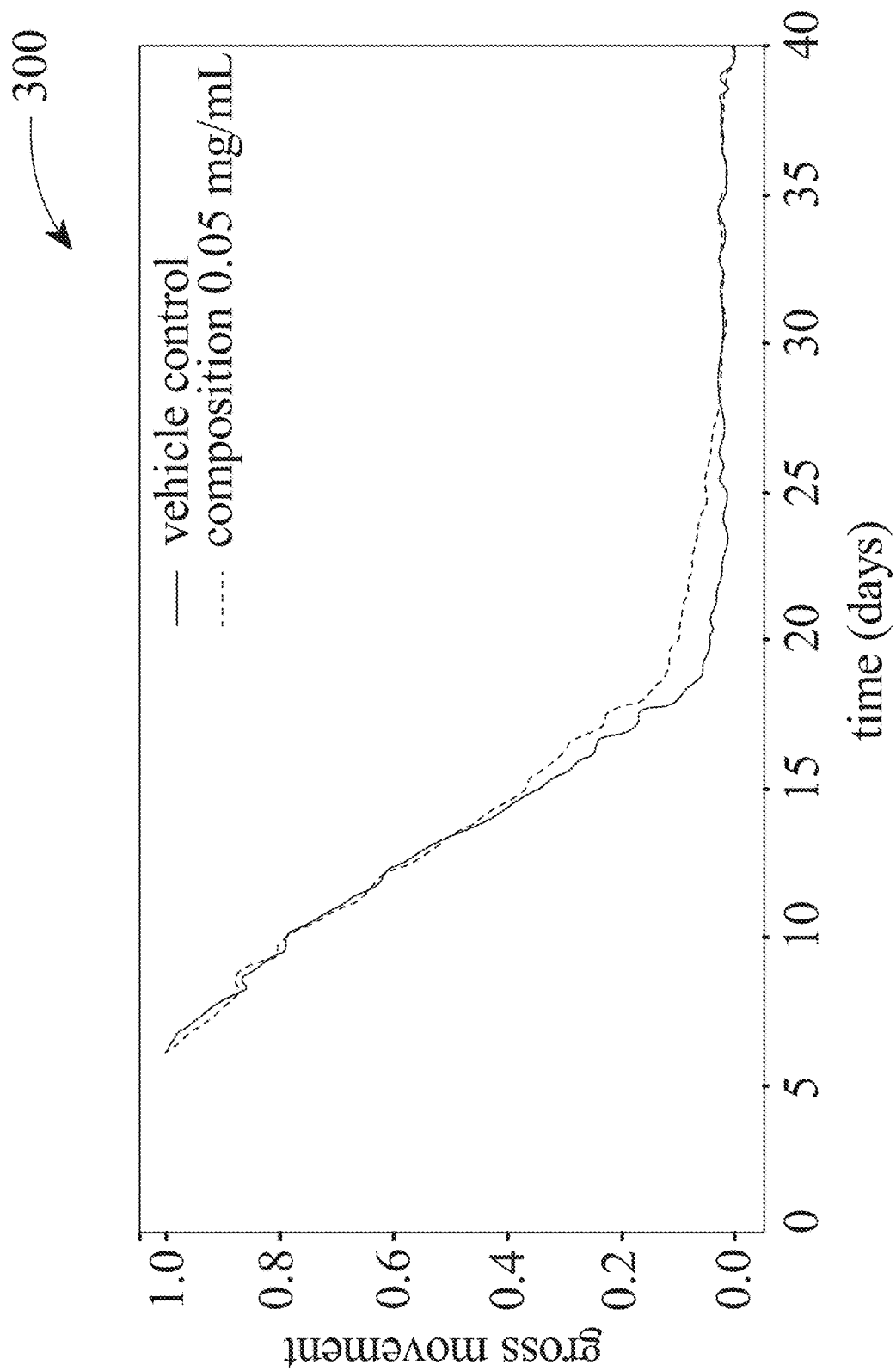
FIG. 3A illustrates a chart illustrating the healthspan effect on *C. elegans* adult animals utilizing the composition.

Referring now to FIG. 3A, is a chart illustrating the healthspan effect on *C. elegans* organisms utilizing composition 100. A "healthspan," as used in this disclosure is the quantified spatial location and movements of organisms during their lifespan. In a non-limiting example, healthspan may include life span free from chronic diseases and disabilities. Materials and methods used to produce this data may include anything as described above in reference to FIG. 2. Organisms treated with the composition 100 at 0.05 mg/ml showed increased activity relative to the vehicle control between days 20 and 28. This result can indicate that the organisms treated with composition 100 retained higher levels of activity late in life had a longer healthspan than the control vehicle and had overall increased quality of life.

Referring now to 3B, is a chart illustrating the healthspan effect on *C. elegans* organisms utilizing composition 100, following the same study procedures as in FIG. 3A. Chart 304 shows the results of composition 100 varying in mg/ml on the healthspan effect on *C. elegans* adult animals when compared to the vehicle control, resveratrol, and rapamycin. Chat 204 illustrates the impact of composition 100 at 0.05, 0.25, and 1.25 mg/ml; resveratrol at 100 μM; and rapamycin at 50 μM.

Figure 3B:
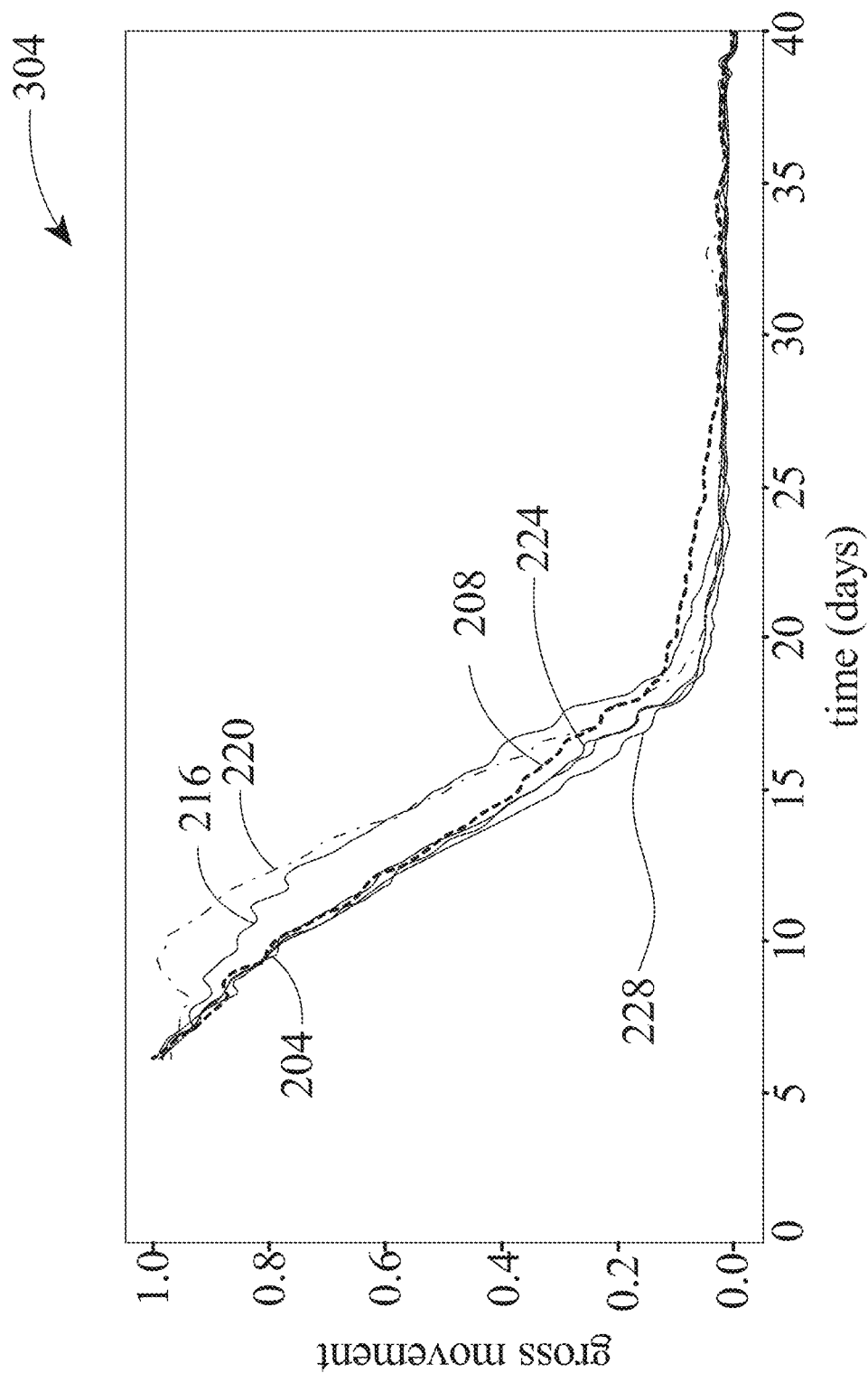
FIG. 3B illustrates a chart illustrating the healthspan effect on *C. elegans* adult animals utilizing the composition.

Still referring to FIG. 3B, treatment with 0.05 mg/mL of composition 100 may increase both lifespan and healthspan in subjects relative to the negative control (P<0.0001). The time at which 50% of the animals have died as shown in Table 1, termed the median lifespan, in the 0.05 mg/mL 208 composition 100 treated animals may increase by more than a day compared to the untreated animals, and they may be more active in their later life. The higher concentrations of composition 100 may show no increase in lifespan relative to the controls. The higher concentrations of composition 100 may tend to promote rapid early growth which may counteract the longevity benefit observed at the lower concentrations. Table 1 shows age in days at which the given percentage of animals are dead, where differences at 25, 50, 75, 90, and 95% mortality relative to the negative control group is shown, where * represents p<0.05.

TABLE 1

| Treatment | No. of Subjects | 25% Mortality | 50% Mortality | 75% Mortality | 90% Mortality | 95% Mortality |
| --- | --- | --- | --- | --- | --- | --- |
| Negative Control | 383 | 21.1 | 24.3 | 26.9 | 29.3 | 30.5 |
| 0.05 mg/mL Composition | 367 | 21.5 | 25.9* | 29.1* | 32.3* | 34.3* |
| 0.25 mg/mL Composition | 380 | 21.3 | 24.6 | 27.3 | 29.2 | 30.3 |
| 1.25 mg/mL Composition | 303 | 20.9 | 23.9 | 26.5 | 28.5 | 29.8 |
| 100 μM Resveratrol | 361 | 22.4* | 25.5* | 28.3* | 30.2 | 32.3* |
| 50 μM Rapamycin | 369 | 24.6* | 29.5* | 32.8* | 35.7* | 36.1* |

Still referring to FIG. 3B, young animals may be sampled after two days of exposure (i.e. *C. elegans* at age 2) and aged animals may be sampled after nine days of exposure to composition 100 (i.e. *C. elegans* at age 9) with both a negative control and positive control (50 μM rapamycin 220). 0.05 mg/mL 208 composition 100 may cause relatively mild changes in gene expression compared to Rapamycin 220. The expression of a small number of genes with established roles in longevity (i.e. biomarker of aging), including hypoxia inducible factor 1, superoxide dismutase, and pha-4, may be significantly affected by composition 100 treatment. composition 100 treatment may produce less disruptive changes compared to that of Rapamycin 220 to established longevity-related genes in *C. elegans*.

Figure 4:
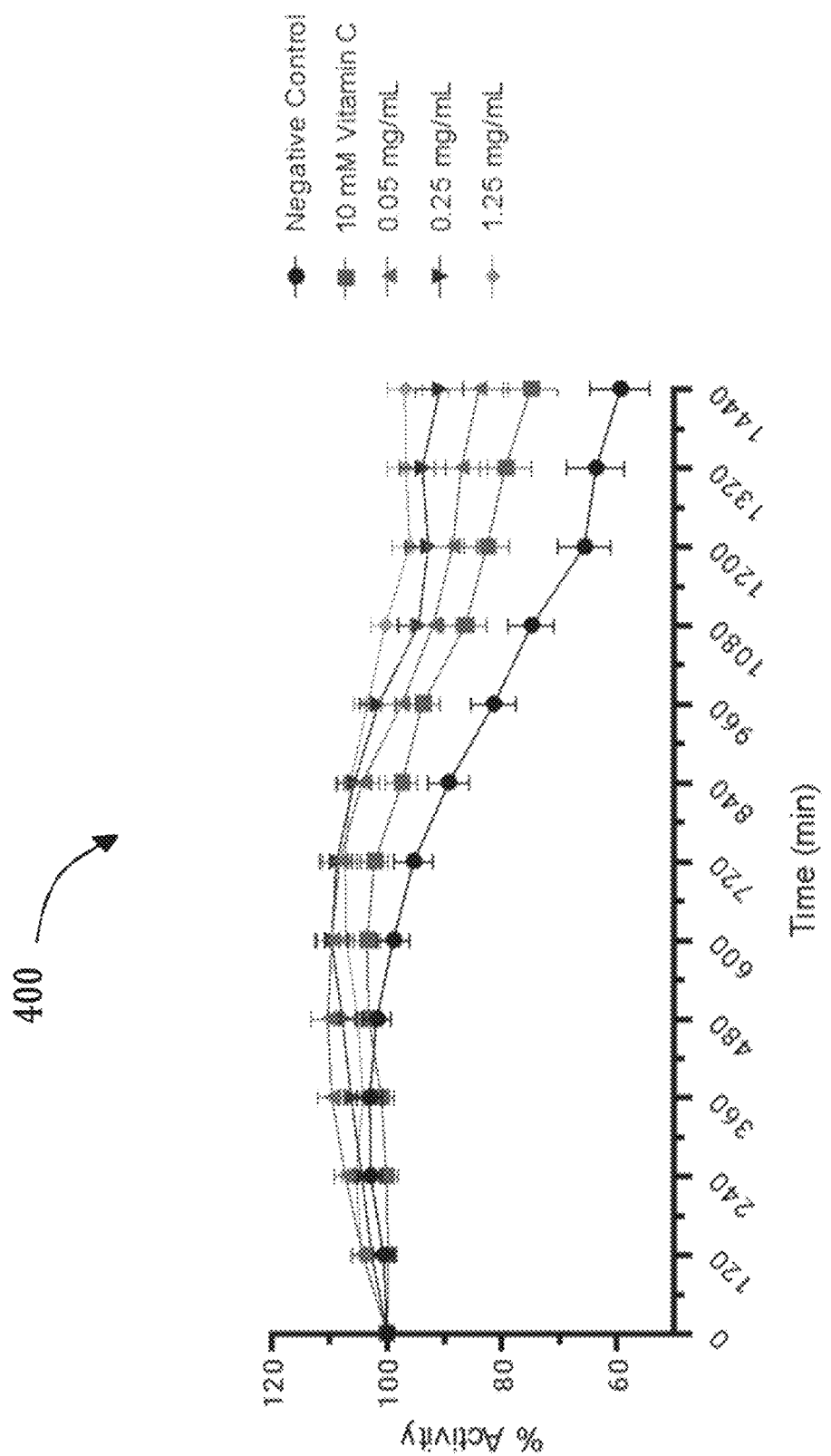
FIG. 4 illustrates an exemplary line graph demonstrating a dose-dependent protective effect when a composition is administered to *C. elegans;*

Now referring to FIG. 4, the figure shows an exemplary line graph demonstrating a dose-dependent protective effect when composition 100 is administered to *C. elegans*. Composition 100 may be administered to *C. elegans* following exposure to 10 millimeters of paraquat, which is a reactive chemical that induces oxidative stress. As a result, composition 100 demonstrates a dose-dependent protective effect. Once exposed to the paraquat, in an embodiment, composition 100 may be separated into five intervention groups to determine the effect: a negative control group, a Vitamin C positive control group, a 0.05 milligram per milliliter sample group of composition 100, a milligram per milliliter sample group of composition 100, and a 1.25 milligram per milliliter sample group of composition 100. Composition 100, as seen in the exemplary chart, may be more protective against oxidative stress than Vitamin C. Furthermore, composition 100 may demonstrate remarkably potent protection against acute physiologic stress induced by oxidative stress. Oxidative stress as described above is a state that occurs when there is an excess of free radicals in a body's cells. The body produces free radicals during normal metabolic processes. Oxidative stress can damage cells, proteins, and DNA, which can contribute to aging. It may also play a role in development of a range of health conditions, including diabetes, cancer, and neurodegenerative diseases such as Alzheimer's. Composition 100 may include and/or act as an antioxidant to counteract and prevent the aging and neurological effects of oxidative stress.

Referring now to FIG. 5, FIG. 5 illustrates a table 500 listing exemplary baseline biomarkers of aging measurement monitored with use of composition 100. Baseline biomarkers of aging may include telomere length 504, C-reactive protein 508, small dense LDL particles 512, homocysteine 516, Hemoglobin A1C 520, vitamin D 524, fasting insulin 528, and immunological tests 532. Additionally baseline biomarkers of aging measurement may include any biomarker of aging described throughout this disclosure, such as mTOR activity 536, insulin-like growth factors 540, 5' AMP-activated protein kinase 544, heart rate variability 548, blood glucose 552, DNA methylation 556, whole-genome sequencing 560, metabolomics 564, redox potential 568, quantitative electroencephalography 572, validated questionnaires 576, and smart device data 580.

Still referring to FIG. 5, biomarkers of aging listed herein may be used to monitor the impact of composition 100 when administered as described further below. Baseline biomarkers of aging measurement listed herein may also be used in generating and modifying the dose schedule of composition 100. "Telomere length," as used herein, is a test used to measure the length of telomeres. "Telomeres," as used in this disclosure, are little cap-like structures on the ends of chromosomes that are responsible for healthy cell function. As time passes, telomeres may become shorter, which may lead to aging and chronic disease. In young humans, telomeres are about 8,000-10,000 nucleotides long. They shorten with each cell division, however, and when they reach a critical length, the cell stops dividing or dies. Regenerative medicine research may involve the regeneration of telomeres to preserve and even restore length. A telomere length 504 test may show how long telomeres take to gain insight into how rapidly or slowly a body is aging. "C-reactive protein," as used in this disclosure, is an inflammatory protein. Inflammation is one primary way disease genes get turned on, and it is generally destructive all over the body. While C-reactive protein 508 may be essential for cleaning up bad bacteria, in excess it may lead to accelerated aging, chronic disease, and damage to the telomeres. Composition 100 may work to keep C-reactive protein 508 levels in the range of <0.5 mg/L. A "small dense low-density lipoprotein particle," as used in this disclosure is a cholesterol protein that carries cholesterol to and away from the body's cells. Small dense low-density lipoprotein (LDL) cholesterol may be a cholesterol protein that increases a person's risk of heart disease if when found in excess. Composition 100 may work to keep small dense low-density lipoprotein particle 512 levels in the range of <200 nmol/L.

Still referring to FIG. 5, a "homocysteine," as used in this disclosure, is a type of amino acid. Homocysteine 516 in excess, especially when coupled with a B vitamin deficiency, may be linked to cognitive decline, which may drastically reduce quality as well as length of life. Composition 100 may work to keep homocysteine 516 levels in the range of <7 Umol/L. "Hemoglobin A1C," as used in this disclosure, is a blood test that measures the average blood sugar levels over the past 3 months. When it is high, it may indicate pre-diabetes or diabetes, and an elevated A1C 520 may be linked with higher rates of all-cause mortality in patients with diabetes. Composition 100 may work to keep Hemoglobin A1C 520 levels in the range of <5.3%. "Vitamin D," as used in this disclosure, is a group of fat-soluble secosteroids responsible for increasing intestinal absorption of calcium, magnesium, phosphate, and many other biological effects. A deficiency in vitamin d 524 may be linked to chronic disease, and optimal levels may be linked to an actual preservation of telomeres, meaning one may live longer and stay healthier. Composition 100 may work to keep Vitamin D 524 levels in the range of 50-60 ng/mL. "Fasting insulin," as used in this disclosure, is a test used to measure levels of insulin in the blood. Higher insulin 528 levels may be linked to insulin resistance and may increase the risk of heart disease, cancer, and Alzheimer's. Composition 100 may work to keep insulin levels 528 in the range of <3 ulU/mL. "Immunological tests," as used in this disclosure, are tests employed to analyze a body's immune system concerning functions and disorders. Even though diseases that appear later in life such as Alzheimer's, may be classified as degenerative diseases, the immune system may play a significant role in the disease process. In some embodiments, immunological tests 532 may include a field of research and/or testing such as cytokine model of cognitive function, anti-nuclear antibodies, complement deficiency assays, C1 inhibitor Function, immunoglobulins, insulin antibodies, ovary antibodies, skin antibodies, and similar tests.

Still referring to FIG. 5, "DNA methylation," as used in this disclosure, is a biological process by which methyl groups are added to the DNA molecule. Methylation may change the activity of a DNA segment without changing the sequence. When located in a gene promoter, DNA methylation may act to repress gene transcription. In mammals, DNA methylation may be essential for normal development and is associated with a number of key processes including aging, and carcinogenesis. DNA methylation levels may be used to accurately estimate the age of tissues and cell types, forming an accurate epigenetic clock. DNA methylation as biomarkers may determine biological age of any tissue across the entire human lifespan, even during development. In some embodiments, using DNA methylation as a biomarker of aging may include a biological age test. "Biological age tests," as used in this disclosure, are tests that determine how old a physical body is, in contrast with a correlating calendar age. They may be used to set a health baseline to measure/monitor the effects of treatments for reversing the effects of aging. For example, biological tests may include, DNA methylation using bisulfite conversion on a *salvia* sample received from a user. "Bisulfate conversion," as used in this disclosure, is a method used to make it easy to distinguish methylated from unmethylated cytosines in genomic DNA at single base resolution. DNA may be first denatured (made single-stranded) and then treated with sodium bisulfite. Sodium bisulfite may selectively change unmethylated cytosines into uracil through deamination, while leaving methylated cytosines (both 5-methylcytosine and 5-hydroxymethylcytosine) unchanged. By then amplifying the treated DNA with polymerase chain reaction (PCR), uracil may be further converted to thymine. At this point all nucleotides that were originally unmethylated cytosines may become thymine while those that were methylated cytosines may remain cytosines. The result may be a clear nucleotide difference between methylated and unmethylated cytosines that may be easily identified by comparison to the original reference genome.

Still referring to FIG. 5, "whole-genome sequencing," as used in this disclosure is the process of determining the entirety of a DNA sequence of an organism's genome at a single time. Genomic information may be instrumental in identifying inherited disorders, characterizing the mutations that drive cancer progression, and tracking disease outbreaks. Whole-genome sequencing may involve isolation of genomic DNA, random fragmentation of genomic DNA, size selection using electrophoresis, library construction, paired-end sequencing (PE sequencing), and genome assembly. In some embodiments, whole-genome sequencing may include human microbiome analysis. "Human microbiome analysis," as used in this disclosure, is the study of microbial communities found in and on the human body. Human microbiome profiling may be used to understand the role of microbes in health and disease.

Still referring to FIG. 5, "metabolomics," as used in this disclosure, is the study of small molecules, commonly known as metabolites, within cells, biofluids, tissues or organisms. Metabolomics may provide biomarkers, such as stool, saliva, serum, and urine as useful for identification of early-stage diseases. In some embodiments, the change in baseline biomarker of gaining measurement may include the change in plasma levels of metabolites, which is the concentration or amount of various metabolites. "Redox potential," as used in this disclosure, is s a measure of the tendency of a chemical species to acquire electrons from or lose electrons to an electrode and thereby be reduced or oxidized respectively. Redox potential is expressed in volts (V). Redox potential related biomarkers may include reactive oxygen species (ROS) levels, molecules that are modified by interactions with ROS, and molecules produced by cells in response to ROS, e.g. antioxidant enzymes, or as by-products. "Quantitative electroencephalography," as used in this disclosure, is s a field concerned with the numerical analysis of electroencephalography (EEG) data and associated behavioral correlates. EEG related biomarkers may include frequency analysis (spectral analysis), significance probability mapping, and other analytic techniques. "Validated questionnaire," as used in this disclosure, a questionnaire/scale that has been developed to be administered among the intended respondents. The validation processes may be completed using a representative sample, demonstrating adequate reliability and validity. Validated questionnaires may include PROMIS Global-10, WHODAS 2.0, and similar questionnaires. "Smart device data," as used in this disclosure, is biometric data received from smart device. Biometrics may include body measurements and calculations related to human characteristics.

Referring now to FIG. 6, is a table 600 listing exemplary baseline biomarkers of aging measurement related to neurodegeneration monitored with use of composition 100. Baseline biomarkers of aging measurement relating to neurodegeneration (i.e. baseline biomarkers of neurodegeneration) may be used to determine the dose schedule 128 of composition 100. Baseline biomarkers of aging measurement relating to neurodegeneration may include Amyloid beta (Aβ) 604, β-site APP-cleaving enzyme 1 gene (BACE1) 608, Soluble Aβ precursor protein (sAPP) 612, Autoantibodies 616, Cerebrospinal fluid biomarkers 620 (i.e., CSF oligomeric α-synuclein, CSF phosphorylated α-synuclein, CSF α-synuclein aggregates, a-Synuclein species in the blood, Lysosomal enzymes, etc.), and any other biomarker of aging related to neurology described throughout this disclosure. "Amyloid beta (Aβ)," as used in this disclosure, is a family of peptides produced by proteolytic cleavage of the type I transmembrane spanning glycoprotein amyloid-beta precursor protein (APP). When Aβ peptide 604 is released by proteolytic cleavage of amyloid-beta precursor protein, some Afl peptides that are solubilized are detected in CSF and blood plasma which makes AB peptides 604 a promising candidate for biological markers. Amyloid beta 604 may be correlated with oxidative stress, altered calcium homeostasis, induction of apoptosis, structural damage, chronic inflammation, and neuronal formation of amyloid has been proposed. "BACE1," as used in this disclosure, is an aspartic acid protease important in the formation of myelin sheaths in peripheral nerve cells. BACE 1 608 activity may contribute to the amyloidogenic process in Alzheimer's disease. "Soluble Aβ precursor protein (sAPP)," as used in this disclosure, is an integral membrane protein whose proteolysis generates beta amyloid ranging from 39- to 42-amino acid peptide. sAPP 612 may play a role during neuroregeneration, and regulation of neural activity, connectivity, plasticity, and memory. Large soluble APP (sAPP) 612 that are present in CSF may serve as a biomarker of Alzheimer's disease. "Autoantibodies," as used in this disclosure, is an antibody produced by the immune system that is directed against one or more of the individual's own proteins. For example, titers of autoantibodies 616 such as anti-beta-amyloid antibodies may be found at lower numbers in the CSF of Alzheimer's patients than neurologically healthy patients. "Cerebrospinal fluid biomarkers," as used in this disclosure, are biomarkers in relation to neuroeducation found in cerebrospinal fluid. Cerebrospinal fluid biomarkers 620 may be correlated to Parkinson's disease, Motor neuron disease, Alzheimer's disease, and other extrapyramidal syndromes.

Figure 7:
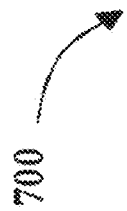
FIG. 7 illustrates a table representing the percentages of biological macromolecules in an exemplary embodiment of the composition.

Now referring to FIG. 7, a table 800 representing percentages of biological macromolecules in an exemplary embodiment of the composition 100 is illustrated. In an embodiment, composition 100 may include a plurality of biological macromolecules comprising, without limitation, amino acids, carbohydrates, cofactors and vitamins, energy, lipids, nucleotide, partially characterized molecules, peptide, fecal matter and xenobiotics. Exemplary percentages by weight are also shown in the figure; percentages may vary by composition. In an embodiment, composition 100 may includes 19% amino acids, 3% carbohydrates, 4% cofactors and vitamins, 1% energy, 26% lipids, 7% nucleotide, 1% partially characterized molecules, 4% peptide, 22% fecal matter, and 13% xenobiotics.

With continued reference to FIG. 7, a pie chart representing an exemplary percentage breakdown by the total weight of the plurality of biological macromolecules 104 in the composition is shown. Plurality of biological macromolecules 104 of composition 100 represent around 20-30% of weight per gram of dried, lyophilized product. Composition 100 overall may be composed of water and lipid-soluble, biological macromolecules, including microbially-derived postbiotics such as secondary bile acids and short-chain fatty acids (SCFAs). In general, composition 100 may include amino acids, bile acids, fatty acids, amino acids-related material, indole derivatives, sugars, carboxylic acid, nucleobase-related material, biogenic amines, vitamins/cofactors, dihydroceramides, glycerophospholipids, triacylglycerols, alkaloids, glycosylceramides, diacylglycerols, cholesterol esters, amine oxides, cresols, acylcarnitine, ceramides, hormones, and other endogenously produced small molecules. The figure itself is an actual percentage breakdown by the total weight of all major biological macromolecules measured from two separate masterbatches of the fecal derived composition analyzed in triplicate on the targeted MxP Quant500 LC-MS/MS assay.

Figure 8:
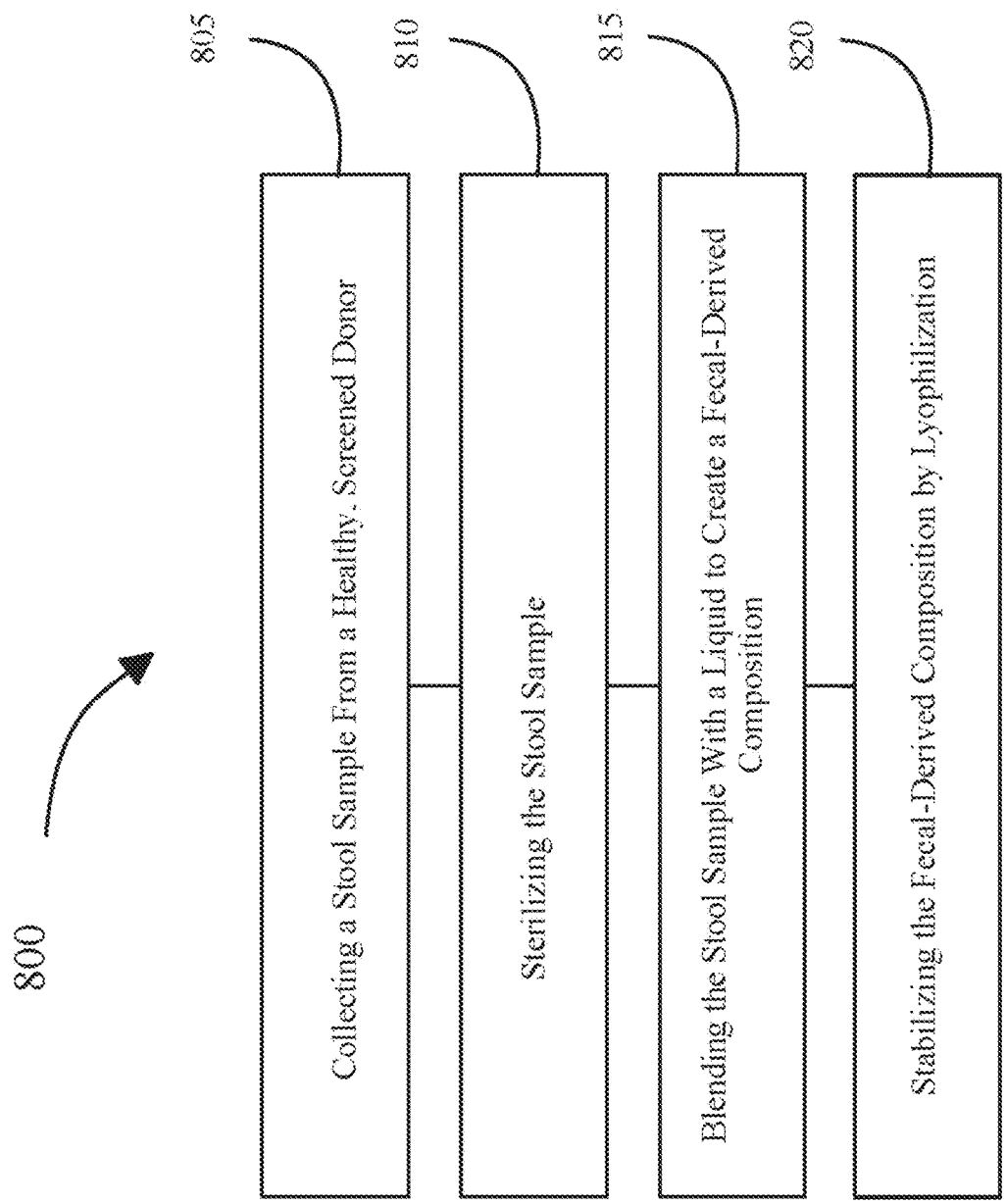
FIG. 8 illustrates a flow diagram of an exemplary embodiment of a manufacturing method for a composition of a fecal-derived sterilized postbiotic.

Now referring to FIG. 8, shown is a flow diagram illustrating an exemplary embodiment of a manufacturing method 800 for a composition 100 of a fecal-derived sterilized postbiotic. Additionally or alternatively, additional disclosure related to manufacturing method for a composition may be found in U.S. Nonprovisional application Ser. No. 17/721,908, filed on Apr. 15, 2022, and entitled "COMPOSITION OF MATTER AND METHODS FOR A FECAL-DERIVED STERILIZED PREBIOTIC AND POSTBIOTIC," the entirety of which is incorporated herein by reference.

Still referring to FIG. 8, at step 805, method 800 includes collecting a stool sample from a healthy, screened donor, wherein the stool sample is frozen. In this disclosure, a "stool sample" is non-sterilized human fecal matter, while the "donor" is the human person the fecal matter comes from. Stool sample may be considered a non-sterilized fecal composition, as explained above. "Frozen" may include the sample being kept at a temperature of between −20 to −80 degrees Celsius for anywhere from 1-10 years. Healthy, screened donors may experience onboarding and routine testing prior to giving the stool sample. A suitable stool donor may be identified using a fecal transplant questionnaire. If the responses meet qualifications additional screening may be performed. Additional screening may include questioning the potential donor in an interview regarding the answers to the questionnaire, obtaining basic health history, or health practices. Potential donors may be "screened" for any presence of infectious disease symptoms and may provide a stool and serum sample for analysis. Potential donor's serum can be obtained to assess for the presence of an HIV strain or for syphilis for example. HIV and syphilis can be retested after three weeks from the initial testing to check and confirm the absence of seroconversion. All serum and stool laboratory testing may be performed by a qualified laboratory. Additionally, stool analysis may include analysis to detect the presence of six Multi-Drug Resistant Organism genes. Testing may be performed in a stepwise manner. In one aspect, stool assessment may be done in less than 14 days. Upon receipt of assessment, if deemed qualified, potential donors are further screened based on a serum sample and provided perianal swabs for both MRSA and CRE. Serum and stool testing may be performed using a certified laboratory. Additional seroconversion studies for the presence of human immunodeficiency virus (HIV) and syphilis may be performed three weeks after initial screening and before release of a donor's fecal material. Donor stool may not be used for capsule production until this information is obtained and confirmed. Overall, the screening determined whether or not the donor is healthy enough to provide the actual stool sample to be used for composition 100. Generally, this pre-donation screening may help ascertain that a potential donor is free from the following non-exhaustive list of afflictions: chronic disease, autoimmune disease, current or past chronic gastrointestinal disease, atopic asthma, atopic dermatitis, diabetes, metabolic syndrome, mood disorders, chronic pain, and/or infectious diseases. Mood disorders considered for treatment or amelioration of a condition include anxiety, depression and obsessive-compulsive disorder. Individual stool samples from the same healthy, screened donor may be combined after sterilization to form a stool batch. Once formed, the stool batch may be sifted to remove any large particulate matters. Donor screening can be performed using various of the criteria described herein in order to identify a healthy donor.

Still referring to FIG. 8, recruitment of a human donor may begin with a short online survey targeting health-conscious communities. For example, in some embodiments, donors may be recruited from a group of individuals who engage in outdoor activities, eat organic foods, and/or generally live a healthy lifestyle. Key aspects of this survey may identify eligibility of donor to give stool samples. For example, but without limitation, donors may be considered eligible when vaginally birthed and breastfed exclusively for 6 or more months. Additionally, another example may be that the potential donor cannot have been diagnosed with a pre-existing condition, such as the ones described above. A potential donor may then be interviewed regarding the donor's diet and lifestyle. Donor screening may also take into consideration food choices, mental health, and their community or the like. Diet and lifestyle factors may also be considered when selecting donors. In some embodiments, an ideal donor may eat a healthy, well-balanced diet and generally engage in healthful practices that support holistic wellbeing of the individual, such as exercise. If a qualified donor remains active, then the donor may be asked to undergo selected tests every six months or earlier depending on a new exposure or illness. Screening questions may include, without limitation: frequency of bowel movements per day/week, how those bowel movements typically rate on the Bristol stool scale, dietary history, relationship with food, whether the potential donor was born vaginally and/or breast-fed, the environment the potential donor was raised in, number and age of sibling(s), exposure to environmental contaminants, treatment for certain types of infections, history of antibiotic use, weight fluctuations, family health history, characteristics about the potential donor's menstrual cycle (if applicable), age, occupation, weight, height, exercise habits, smoking habits, drinking habits, sexual history, exposure to STIs, illicit drug use, recent tattoo/piercing history, hospitalization, surgery history, medical diagnosis history, mental health, allergies, international travel, prescription and/or supplement use, microbiome history, and more. Donors may also be screened for one or more of the following pathogens or a species falling within bacterial pathogens, parasites, viruses and fungi pathogens, or antibiotic resistant genes.

Still referring to FIG. 8, another screening example for potential donors may include multiple phases. For example, phase 1 of the screening may include an assessment of the donor's serum involving a complete blood count (CBC) with differential, a comprehensive metabolic panel (CMP), a hemoglobin A1C (HgAlC), and antibodies for HIV-1 and HIV-2. Phase I for screening the stool may also include 16s diversity index sequencing, obtaining a metabolomics profile, O&P with giardia antigen, and culturing the stool for the presence of *Salmonella, Shigella, Campylobacter*, and EHEC. Phase 2 of the exemplary screening can occur approximately every six months or after new onset symptoms or a change in risk factors for the donor occurs. Serum at this stage would be tested for CBC with differential and CMP. These phases may or may not immediately follow each other, and phases may be modified as needed. Generally, the frequency and timing of testing will vary depending on the illness or exposure being tested for. HIV and syphilis, for instance, may be retested several weeks after the initial test to check for seroconversion. Follow-up testing for hepatitis B and C may also be useful. No donor stool should be used for powder and/or capsule production until all testing information is complete and confirmed. Some tests may also be repeated every six months throughout the donation time period as an extra safety precaution. Testing may be optional given sterilization of the sterilized fecal-derived postbiotic composition. Additionally, the physical exam portion of the screening may be another phase. An exemplary physical exam list may include, without limitation, as follows: capillary refill, assess for clubbing and peripheral cyanosis, assessment of cranial nerves, inspection of conjunctiva, lips and buccal mucosa, inspection of neck for appearance, symmetry, trachea position, and masses, palpation of the thyroid for enlargement, tenderness and masses, visual assessment of respiratory effort and signs of central cyanosis, lung auscultation, carotid auscultation, cardiac auscultation and palpation, and other similar inspections for the rest of the donor's body.

With continued reference to FIG. 8, although the mental health of a potential donor may be difficult to measure quantitatively, it may be possible to obtain a good sense of the suitability of a potential donor through careful screening of health, personality, and temperament, in addition to asking comprehensive intake questions, performing infectious disease testing, and performing physical examinations. This extensive vetting process may allow a physician to identify potential risk factors associated with a potential donor's lifestyle and overall health. In some embodiments, initial donor screening may be conducted by phone interview to cover basic health history and health practices. If a potential donor passes the phone interview, then a next step in the vetting process may be to follow up with an in-person or remote video interview (e.g., telehealth consult) to review and confirm the potential donor's answers to the intake questionnaire. A next step may then include screening the potential donor for infectious disease, followed by a further step of performing a physical exam on the potential donor, or having them obtain one from their local physician if a remote donor.

Continuing to refer to FIG. 8, once a donor is approved, said donor may receive a set of detailed donor instructions. Donor instructions advise the donor on what to do in order to give stool samples. The instructions may include recommendations for maintaining a healthy microbiome through diet and lifestyle practices. For example, a donor may be instructed to eat an organic, whole foods-based diet that consists of varied fruits and vegetables, and to drink enough water to stay hydrated. A donor optionally may be instructed to engage in body movement each day, which may take the form of housework, gardening, walking, biking, etc. Such movement may be useful in maintaining a healthy microbiome in the donor. Donor instructions may include symptoms that the donor must report as post-screening approval. For example, the donor may be instructed to immediately notify the FMT service provider if the donor experiences any change in bowel habits; sign of cold, flu, or fever; change associated with risk of HIV or hepatitis contraction (e.g., change in sexual practices, blood transfusion, needle stick incidence, new tattoos); use of antibiotics, etc. Donor instructions may also include which types of stool samples are acceptable based on the Bristol Stool Scale or any other suitable stool chart, as well as other information on safe collection, handling, and delivery of stool samples. The donor may also be instructed to avoid contamination of stool with urine, and to notate where the collected stool falls on the Bristol stool scale, along with the date and time of collection. Donor instructions may also include instructions on amount, color, type, etc. of stool sample.

With continued reference to FIG. 8, in some embodiments, once the stool sample is collected, the method may include freezing the stool sample immediately after collection. Freezing may be accomplished in several ways, such as, but not limited to: flash freezing, in a regular freezer, or freeze-drying via sugar crystallization or lyophilization. Freezing of the stool sample may be done at $-6°$ C. to $-80°$ C. The ability to freeze, store, and then transport to then thaw for manufacturing allows for various advantages. Traditionally, non-sterilized FMT may be processed within twelve to twenty-four hours of donation with fresh stool samples. When the live bacteria are the focus of the end-product, this represents an obvious requirement. Stool samples may be selected from multiple donors less than 24 hours before processing, with each donor contributing approximately 2,100 grams of fresh stool. Stools samples may be prioritized for use based on date. Selected stools may be left to thaw at 4 degrees Celsius overnight. Each thawed stool may be opened under a Class IIA biosafety cabinet for the first time since being sealed by the donor at the time of collection and is placed in a self-sealing, glass autoclave vessel. In some embodiments, donors may be required to freeze their own stool samples. Further, by having donors freeze multiple stools at home, not only does this increase convenience in bulk pick-ups, but also may allow a greater donor population geographically. Donors may no longer be limited by location. This method may also provide a decentralization of the stool banks with the capacity for reduced human interaction. In some embodiments, stool samples may be collected, frozen, and couriered on dry ice to a processing location.

Still referring to FIG. 8, composition 100 may provide enhanced safety and efficacy over non-sterilized FMT therapies. As used herein, a "fecal microbiota transplantation (FMT)" is a process of transferring fecal material from one subject to another subject. Non-sterilized fecal microbiota transplant therapy has provided a unique example of how microbial dysbiosis in the gastrointestinal (GI) tract can be improved in order to treat disease. Generally, the transplantation process uses non-autologous fecal matter. The fecal microbiota (or fecal transplant) is generally obtained from a healthy, screened donor, as explained above, and is administered into the colon of a recipient. The process can also be also referred to as microbial transfer therapy, microbiota restoration therapy, intestinal microbiota transfer, donor feces infusion, stool transplant, or fecal bacteriotherapy. As used for the compositions and methods described herein, an FMT product is defined as a fecal pellet derived from a screened donor stool that is processed into a concentrated bacterial pellet. In all instances, "FMT" and "fecal microbiota transplantation" indicate a sample that has not been sterilized and contains live bacteria and viruses. The compositions minimize the risk of transmitting infection from donor stool to a recipient of an FSP capsule or batch of capsules. As with any medical procedure, there are both known and unknown risks associated with non-sterilized FMT. These risks are commonly associated with infectious organisms and/or substances in donor stool that were not identified through screening. Safety concerns regarding infectious disease are particularly worrisome for immunocompromised patients (e.g., patients having AIDS, cancer, diabetes, certain genetic disorders; patients who are malnourished). In addition, the transmission of novel viral and parasitic pathogens, like SARS-CoV-2, through live FMT transfer remains of serious concern. FMT remains with risks and potential side effects for the patient receiving the transfer. Much, but not all, of these risks relate to transmitting infection from the donor stool to the recipient. Such risks may be mitigated, but cannot be completely eliminated, even by extensively screening donors prior to stool collection to minimize the risk of exposing the recipient to a known infectious disease or other risk factors. Moreover, a fecal-derived sterilized postbiotic composition as described herein can be used to shift disease states from diseased to healthy when administered to a subject in a therapeutically effective dose. The shift therefore is not linked to a bacterial species-specific mechanism that occurs through the transfer of a live or non-sterilized FMT.

With continued reference to FIG. 8, optionally, once the stool sample is prepared, a tracking protocol may be implemented. For example, a processed stool sample can be given a batch ID number. The ID number may connect each product with its specific processing date, contained in a written database that includes important information, such as, but not limited to the date and time the stool was collected and processed, total volumes of material used, identity of the donor and the processing technician, the specific gram/capsule measurements, and so on. Optionally, the tracking may also comprise a full log of such information for safety and quality control. Additionally, in some embodiments, at least one sterilized fecal composition product from each batch may be saved for quality control tracking. Stool samples may then undergo freezing, thawing, sterilization, and then be freeze-dried such that they are suitable for oral consumption by their intended recipient, as explained further below.

Still referring to FIG. 8, at step 810, method 800 includes sterilizing the stool sample. The sterilization step of the methods described herein may be performed prior to blending the stool or after blending the stool or after removal of fiber and particulates, as further explained below. As used herein, the term "sterilize" means to remove or kill all bacteria, viruses, and other living organisms from a sample such as composition 100. Sterilization of the stool sample may kill bacteria and/or viruses while retaining bacterial plurality of biological macromolecules 104. In some embodiments, sterilization may be performed using any of the following non-exhaustive means of sterilization: UV-C light, ozone, sonication, microwave irradiation, pasteurization, autoclaving, tyndallization, steam sterilization, flash sterilization, low-temperature sterilization technologies, filtration, dry-heat sterilization, performic acid, glass bead sterilizer, liquid chemicals, ionizing radiation, gaseous chlorine dioxide, vaporized peracetic acid, infrared radiation and/or any other suitable sterilization technique. In some embodiments, the sterilized fecal product may then be stabilized using a freeze-drying technique also known as lyophilization or cryodesiccation. Sterilization may include the method of autoclaving. In this disclosure, "autoclaving" is a sterilization method that uses high-pressure steam. For example, but without limitation, stool sample may be placed in a chamber, an autoclave, or the like. Temperature and pressure of the chamber is increased to a certain level to create the steam to kill the bacteria and microbes. The step may be performed between about 121 to 84 degrees Celsius for approximately 30 minutes. Autoclaving may also be performed between 85 to 140 degrees Celsius for approximately 20 minutes. The pH of the product may be checked prior to the freeze drying technique, and if the pH is below a specified level, another solution may be added to get the pH to that specified level. For example, if the pH measures 6.0, NaOH may be added to increase the pH from about 6 to about 9.0, or higher than 6.5, or 7.0, or 7.5 or 8.0. By increasing the pH at this stage, improves the ability to maintain short chain fatty acid plurality of biological macromolecules 104 of the sterilized fecal-derived postbiotic during lyophilization. Lyophilization or freeze-drying allows the sterilized fecal product to be preserved in a condensed dry powder that is stable for storage and use at room temperature. The lyophilized sterilized fecal-derived postbiotic powder may then be used for oral, topical, vaginal or rectal intake, intranasal administration, or other formulations for intravenous or parenteral administration as contemplated herein.

With continued reference to FIG. 8, while non-sterilized FMT derived products contain live bacteria, the products and composition 100 described herein may not. The sterilized products, extracts and components derived from the products provide a living-organism free composition that is safe for administration. In one embodiment, it is contemplated that the sterilized fecal derived postbiotic composition described herein can be used as an adjuvant in conjunction with non-sterilized FMT products containing living organisms or synthetic communities of gastrointestinal associated bacteria. The compositions described herein can also be used as a stand-alone composition for administration to treat or ameliorate a condition or in combination with other therapeutics. The sterilized fecal-derived postbiotic composition can normalize an environment in a subject in need thereof by allowing existing bacteria to colonize normally eventually supplanting a disease-associated dysbiotic colonization. The sterilized fecal-derived postbiotic composition described herein is also inherently safer because they eliminate infectious disease risk. This is true for both oral ingestion of the material or topical application. Stool contains bacteria that can overgrow. This overgrowth can cause imbalance in both the gut and on the skin. Bacterial overgrowth on the skin, for example, can cause a topical infection. Sterilization of the fecal-derived postbiotic composition, such as via autoclaving, definitively kills all bacteria and viruses while retaining bacterial plurality of biological macromolecules 104.

Still referring to FIG. 8, at step 815, method 800 includes blending the stool sample with a liquid to create a fecal-derived composition. The liquid may include water, such as but not limited to distilled water, water for injection, filtered water, purified water, and/or a buffer and the like. In this disclosure, a "buffer" is an aqueous solution consisting of a mixture of a weak acid and its conjugate base, or vice versa. Its pH, or its acidity, changes very little when a small amount of strong acid or base is added to it, meaning it maintains a constant hydrogen ion concentration. Buffers may be able to neutralize small amounts of added acid or base, thus maintaining the pH of the solution relatively stable. Maintaining the pH of a solution, especially in composition 100, is important because if the pH value of a solution rises or falls too much the short chain fatty acids are volatilized during the lyophilization step. Buffer may include, without limitation, water, a phosphate buffered saline solution, or maldextrin-trehalose solution. Effective ratios of stool to buffer solution may vary, and such variance may depend on the how the stool falls on the Bristol stool scale (or any other such classification system for stool). For example, a blend of approximately 100 grams of stool with approximately 500 milliliters of phosphate-buffered saline (PBS). This 100 gram to 500 milliliters ratio may be suitable for donor stool that is considered to be a "4" on the Bristol stool scale. Other ratios may be more suitable for donor stool that falls elsewhere on the Bristol stool scale. For instance, it may be suitable to add approximately 700 milliliters of buffer solution to 100 grams of donor stool that is classified as a "3" on the Bristol stool scale. In other words, the drier the donor stool is, the greater the amount of buffer solution that may need to be added to the donor stool. After a buffer solution is added to the donor stool in a suitable container, the mixture should be blended to produce a slurry, or semiliquid mixture. The time spent blending may vary depending on the type of blender used, but generally the slurry may be produced in approximately one minute with a sterilized electric blender. Blending the stool sample with a buffer may further include a pH adjustment. A "pH adjustment", in this disclosure, is a change to the acidity and/or basicity of the solution, or stool sample, before combining it with the liquid. Since the buffer allows for little change in the pH level, a pH adjustment may be required beforehand to have the stool sample be at a desired pH level for blending. pH may be adjusted after the stool has been blended with the liquid; at this point the composition may be acidic and so the pH may be titrated up to a pH of 9 using sodium hydroxide that is either 0.5 molar or 1 molar. Moreover, blending the stool sample with a buffer may also involve the use of a comminution device. A "comminution device" is an apparatus that reduces solid materials from one average particle size to a smaller particle size. Comminution device breaks particles of the sample and buffer down so blending of stool sample and the buffer is facilitated. Comminution device may be selected from a group consisting of a crushing device that crushes the solutions before combining them, a grinding device that grinds the sample and buffer before combining them, and a homogenization device that blends the solutions into a homogenous mixture. Comminution device may be any kind of apparatus capable of breaking up, crushing, grinding, cutting, or vibrating particles, such as a mill, crusher, hammer, mallet, or the like.

In some embodiments, the resulting fecal-derived composition may then undergo a form of filtration to separate the large fiber particles from the bacterial and other small molecule components of the stool material. In some embodiments it may then be further concentrated into a microbial pellet. Filtration methods may include centrifugation, vacuum filtration, sieve filtration using gravity, or other mechanistic filtration methods as further explained below. A prepared fecal-derived composition may undergo at least two centrifuge cycles, a first cycle may be used to remove fibrous particulate from the stool-diluent slurry after blending the stool with a buffer. Although any number of centrifuges may be suitable for this step, an example of appropriate equipment may be a Thermo-Fisher Sorvall ST 40 centrifuge suitable for use with 50-milliliter conical tubes. If using such a centrifuge or similar, the slurry may be poured into several 50-milliliter centrifuge conical tubes. In some embodiments, the slurry may be centrifuged for approximately fifteen minutes at approximately 2000 rotation per minute (RPM) or any other suitable RPM. The primary purpose of the first centrifuge cycle is to separate a first fiber pellet from the supernatant, so the time and RPM may vary. The first fiber pellet may be properly and sanitarily discarded, so that the remaining supernatant may be used in the second centrifuge cycle or for processing into the final product.

Still referring to FIG. 8, at step 820, method 800 includes stabilizing the fecal-derived composition by lyophilization. In this disclosure, "stabilize" refers to the ability to resist attachment by chemical action; the solution is in equilibrium. Stabilization may be performed by a method called lyophilization. "Lyophilization" is a process of freeze drying wherein the composition is frozen, lowering the pressure, then the ice is removed by sublimation. Sublimation may be used to make food items more stable, more dissolvable in water, or is used as a late-stage purification procedure, like herein. In other words, lyophilization uses freezing to dehydrate the fecal-derived postbiotic composition. Lyophilization may be beneficial since the process maintains nutrients in the compositing as well as giving the composition a longer shelf life. The method also may optionally adjust the pH of the fecal-derived postbiotic composition is adjusted to about 6.0 to about 9.0 prior to lyophilization. For example, but without limitation, a blended, pH-adjusted, sterilized stool batch may be poured into stainless steel sheet trays, wherein each tray may contain approximately 1 liter of stool slurry. These trays may then be placed into a Millrock Stellar Laboratory Freeze Dryer machine, which runs a freeze-drying cycle for approximately 48 hours. Each tray may have a moisture probe that monitors moisture content throughout the run, ensuring that the batch is dried evenly. The freeze-dried powder may then be removed from the freeze-dryer. Samples from each tray could be removed or measured again for moisture content. Moisture content of less than 8% may be considered acceptable. If a batch finishes above 8%, it may be discarded. The powder from all five trays may then be combined, mixed briefly in the commercial food blender, and then sieved for rough filtration of gross particulates to create a single batch. The final powder may be light brown with a fluffy texture and a characteristic earthy odor. To account for interindividual differences in composition, three separate batches from three donors may be combined and assigned a masterbatch ID (e.g., MB001). The powder may then be stored at 4 degrees Celsius until it is encapsulated.

Still referring to FIG. 8, method 800 may further include removing fiber and particulate matter from the fecal-derived sterilized composition to produce a fecal-derived sterilized prebiotic and postbiotic. "Fibers" in this disclosure are dietary materials containing substances, such as cellulose, that are resistant to the action of digestive enzymes while "particulate matter" is other particles that may limit proper mixing of dried material. Removing fiber and particulate matter from the fecal-derived sterilized composition may then make composition 100 edible and usable. Removing fiber and particulate matter from the fecal-derived sterilized composition may include a combination of removal methods. Combination of removal methods may include filtration. In this disclosure, "filtration" is physical separation process that separates solid matter and fluid from a mixture using a filter medium that has a complex structure through which only the fluid can pass. For example, to separate coffee liquid from the coffee grounds, the mixture is poured over a coffee filter. Other methods of separation that may be used to separate fibers and particulate matter from include, without limitation, centrifugation, sieve filtration, membrane filter press drying, sublimation, flotation, distillation, freezing, chromatography, crystallization, or a combination thereof. If centrifugation is used to prepare the sterilized fecal-derived postbiotic, then the blended stool sample and buffer may be poured into sterilized vials or tubes suitable for use in a centrifuge and undergo at least one centrifugation cycle. Next, the vials may be removed from the centrifuge so that the fiber and large particulate matter pellets may be discarded. A supernatant from the at least first cycle may be poured into new sterilized containers, wherein a "supernatant" denotes the liquid lying above a solid residue after crystallization, precipitation, centrifugation, or other processes. This removal process may be a single step process or can involve one or more of these methods in sequence.

With continued reference to FIG. 8, in other embodiments, the resulting composition after blending may be filtered using another filtration process that is not centrifugation, but rather physical filtration using filter paper or mesh straining. Further processing steps may include the concentration of the supernatant into a bacterial pellet with the option of additional centrifugation. The bacterial pellet obtained after removal of the initial fiber and large particulate removal may be resuspended, for example, at a 1:1 ratio with the fecal supernatant.

Still referring to FIG. 8, method 800 may also include encapsulating the fecal-derived sterilized prebiotic and postbiotic. Herein, "encapsulate" means to enclose something as if in a capsule or the like. Composition 100 may be encapsulated a plurality of ways depending on if the composition is in a solid or liquid form. Composition 100 may be encapsulated in a solid, an aerosol, a pill, a capsule, a tablet, a paste, a powder, a gel, a lotion, a liquid, an injectable, a parental, a buccal, a sublingual, a nasal, a suppository, or a body wash. Encapsulated formulations can be stored at approximately 20, 5, −20 to −80 degrees Celsius. Some examples of encapsulation methods may include, without limitation, spray drying, spray cooling, extrusion, coacervation, lyophilization and emulsification. It may also be formulated into a food or food product, nutraceutical, supplement, dietary supplement, or other form for oral ingestion. The liquid or lyophilized FSP may be added to a beverage, including a sports beverage. It can be formulated for vaginal or rectal implantation or for administration to a sinus passage via spray or gel. Additional stabilizers may be added to the composition. A stabilizing filler may be added to the oral powder or encapsulated form, such as, but not limited to collagen, glutamine, fiber (e.g., inulin, slippery elm, *psyllium*, chia, flax), or carminatives (e.g., ginger, fennel, rose, licorice, peony). A stabilizing filler may also provide additional benefits to a recipient as a prebiotic, but additional benefits are not necessary as a sterilized fecal composition may be the more important factor in effective treatment of the patient. Effective dose size of composition 100 may vary from as small as about 0.25-0.50 milliliters to about 7.5-15 milliliters of a sterilized un-lyophilized frozen liquid fecal-derived composition. Effective dose sizes for lyophilized powder fecal-derived sterilized composition may vary from as small as about 10 milligrams to about 5 grams.

Figure 9:
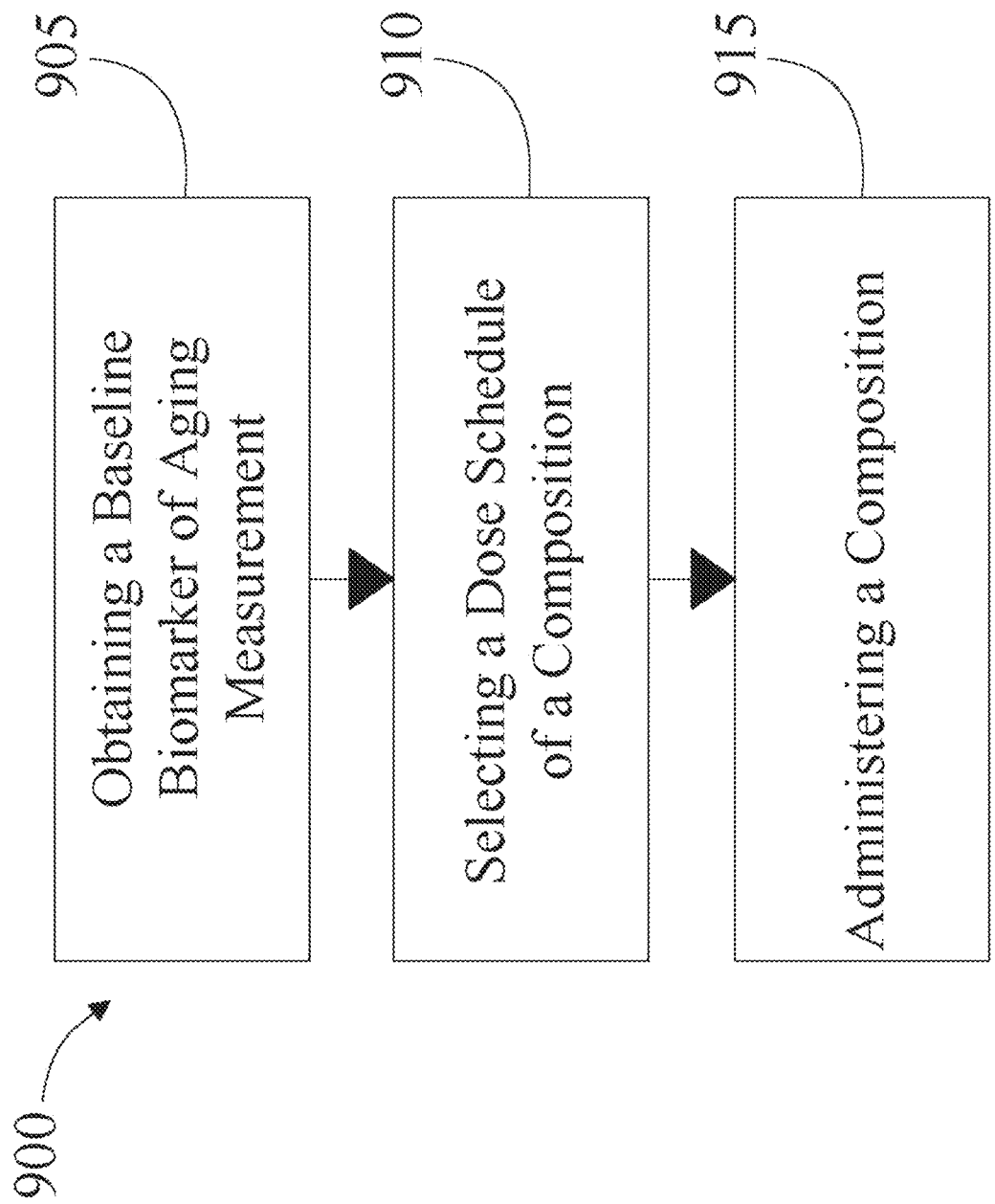
FIG. 9 illustrates a flow diagram of an exemplary method for analyzing an anti-aging effect of composition of a fecal derived sterilized postbiotic.

Referring now to FIG. 9, a flow diagram of an exemplary method 900 for analyzing an anti-aging effect of composition of a fecal derived sterilized postbiotic is illustrated. Method 900 includes a step 905 of obtaining a baseline biomarker of aging measurement, wherein the baseline biomarker of aging measurement includes a biomarker of aging. In some embodiments, the baseline biomarker of aging measurement may include a baseline biomarker of neurodegeneration. These may be implemented as described with respect to FIGS. 1-13.

Still referring to FIG. 9, method 900 includes a step 910 of selecting a dose schedule from a plurality of dose schedules of a composition for a fecal derived sterilized postbiotic as a function of a baseline biomarker of aging measurement, wherein the composition includes a plurality of biological macromolecules including at least a short chain fatty acid, wherein the short chain fatty acid includes acetic acid, propionic acid, and butyric acid and a plurality of agents, wherein the plurality of agents is configured to regulate the biomarker of aging. In some embodiments, the plurality of agents may be configured to regulate blood glucose levels. In some embodiments, the plurality of agents may be configured to regulate heart rate variability. In some embodiments, the plurality of agents may include a co-emulsifying agent. In some embodiments, the plurality of agents may be configured to activate 5' AMP-activated protein kinase. In some embodiments, the composition may be configured to reduce oxidative stress. In some embodiments, the composition may be configured to increase healthspan. In some embodiments, the composition may be configured to treat neurological disorders. These may be implemented as described with respect to FIGS. 1-13.

Still referring to FIG. 9, method 900 includes a step 915 of administering a composition to a subject. In some embodiments, method 900 may further include analyzing a change in the baseline biomarker of aging of the subject using mRNA sequencing. These may be implemented as described with respect to FIGS. 1-13.

Figure 10:
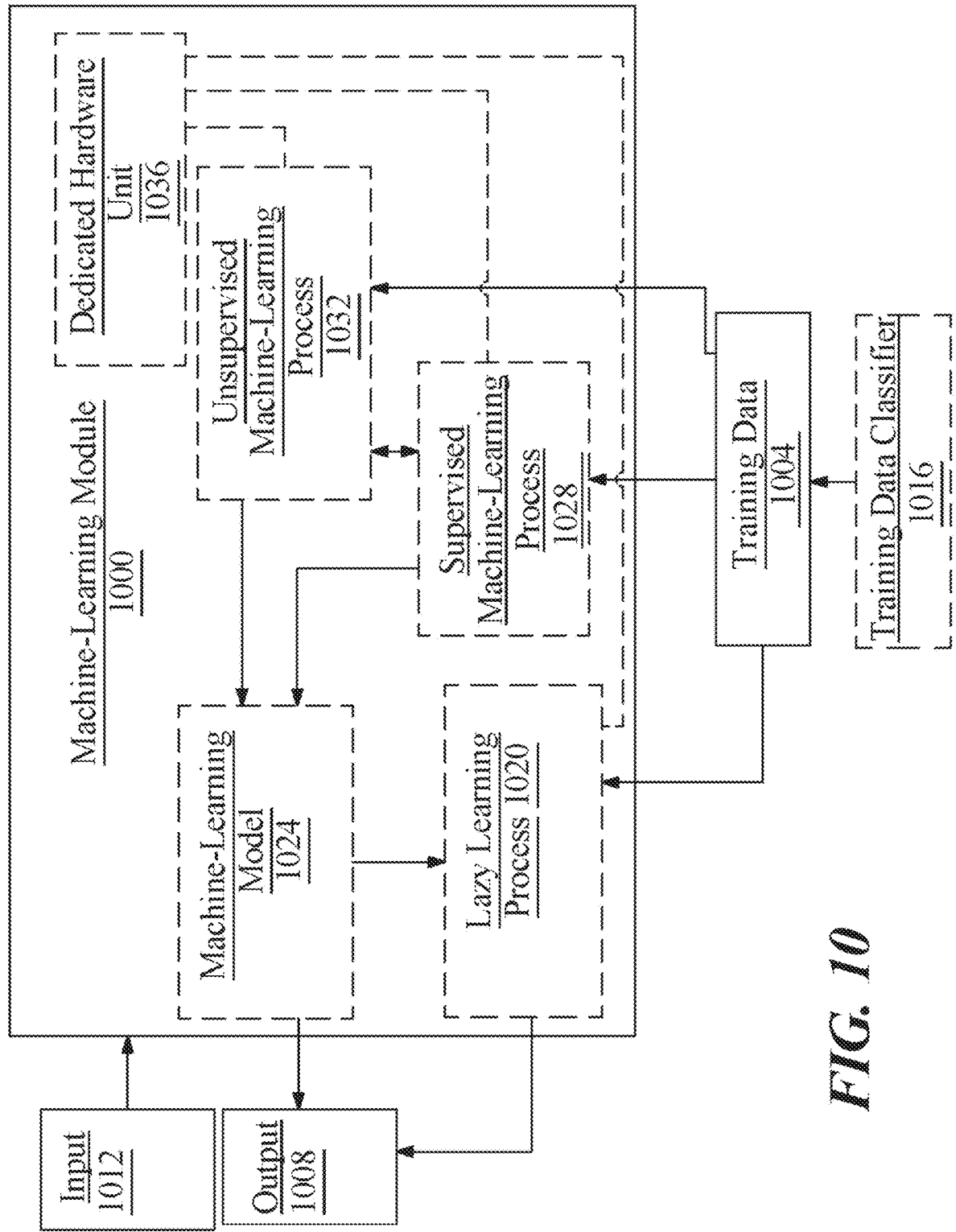
FIG. 10 illustrates a block diagram of exemplary embodiment of a machine learning module.

Referring now to FIG. 10, an exemplary embodiment of a machine-learning module 1000 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 1004 to generate an algorithm instantiated in hardware or software logic, data structures, and/or functions that will be performed by a computing device/module to produce outputs 1008 given data provided as inputs 1012; this is in contrast to a non-machine learning software program where the commands to be executed are determined in advance by a user and written in a programming language.

With continued reference to FIG. 10, in some embodiments, the use of machine learning model may solve technical problems or improve technical processes. In a non-limiting example, the use of machine learning model may improve identifying hidden patterns, correlations, or anomalies that may be difficult for humans to detect. This may enhance the accuracy and efficiency of decision-making processes. In another non-limiting example, machine learning model may enable the automation of tasks that would otherwise require significant manual effort or expertise. By leveraging machine learning model, computing device may automatically process, analyze, and interpret large volumes of data, reducing the time and resources required for manual analysis and improving the overall efficiency of the technical process. In another non-limiting example, the use of machine learning model may enable analyzing data and making decisions in real-time or near real-time, allowing computing device to respond quickly to changing conditions or dynamic environments. In another non-limiting example, machine learning model may learn from individual user preferences, behaviors, or feedback (i.e. user input to personalize and customize the technical process. For example, and without limitation, machine learning model can analyze baseline biomarker of aging measurement, the change in baseline biomarker of aging measurement, or the like to provide tailored analysis or recommendations, optimize settings, or adapt the process to individual needs. This enhances user experience and satisfaction. In another non-limiting example, machine learning model may learn from historical data and generate predictive models that forecast future outcomes or trends predict events, identify potential failures or risks, optimize resource allocation, anticipate customer behavior or determine optimal solutions. This proactive approach may enable better planning, resource management, and decision-making. These may be consistent with any machine learning model described in this disclosure.

Still referring to FIG. 10, "training data," as used herein, is data containing correlations that a machine-learning process may use to model relationships between two or more categories of data elements. For instance, and without limitation, training data 1004 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 1004 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 1004 according to various correlations; correlations may indicate causative and/or predictive links between categories of data elements, which may be modeled as relationships such as mathematical relationships by machine-learning processes as described in further detail below. Training data 1004 may be formatted and/or organized by categories of data elements, for instance by associating data elements with one or more descriptors corresponding to categories of data elements. As a non-limiting example, training data 1004 may include data entered in standardized forms by persons or processes, such that entry of a given data element in a given field in a form may be mapped to one or more descriptors of categories. Elements in training data 1004 may be linked to descriptors of categories by tags, tokens, or other data elements; for instance, and without limitation, training data 1004 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 10, training data 1004 may include one or more elements that are not categorized; that is, training data 1004 may not be formatted or contain descriptors for some elements of data. Machine-learning algorithms and/or other processes may sort training data 1004 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 1004 to be made applicable for two or more distinct machine-learning algorithms as described in further detail below. Training data 1004 used by machine-learning module 1000 may correlate any input data as described in this disclosure to any output data as described in this disclosure. As a non-limiting illustrative example, input data may include baseline biomarker of aging measurement, the change in baseline biomarker of gaining measurement, or the like as described above. As another non-limiting illustrative example, output data may include an efficacy rate of composition 100 or aging rate of a subject.

Further referring to FIG. 10, training data may be filtered, sorted, and/or selected using one or more supervised and/or unsupervised machine-learning processes and/or models as described in further detail below; such models may include without limitation a training data classifier 1016. Training data classifier 1016 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 1000 may generate a classifier using a classification algorithm, defined as a processes whereby a computing device and/or any module and/or component operating thereon derives a classifier from training data 1004. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to different demographic facts of subject. For example, and without limitation, training data classifier 616 may classify elements of training data to different age, gender, smoking, drinking, obesity, stress, exercise, sleep, overall health, and the like.

With further reference to FIG. 10, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 10, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 10, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 10, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 10, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 10, machine-learning module 1000 may be configured to perform a lazy-learning process 1020 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 1004. Heuristic may include selecting some number of highest-ranking associations and/or training data 1004 elements. Lazy learning may implement any suitable lazy learning algorithm, including without limitation a K-nearest neighbors algorithm, a lazy naive Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 10, machine-learning processes as described in this disclosure may be used to generate machine-learning models 1024. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 1024 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 1024 may be generated by creating an artificial neural network, such as a convolutional neural network comprising an input layer of nodes, one or more intermediate layers, and an output layer of nodes. Connections between nodes may be created via the process of "training" the network, in which elements from a training data 1004 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 10, machine-learning algorithms may include at least a supervised machine-learning process 1028. At least a supervised machine-learning process 1028, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include baseline biomarker of aging measurement, the change in baseline biomarker of gaining measurement, or the like as described above as inputs, efficacy of composition 100 or aging rate of a subject as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 1004. Persons skilled in the art, upon reviewing the entirety of this disclosure, will be aware of various possible variations of at least a supervised machine-learning process 1028 that may be used to determine relation between inputs and outputs. Supervised machine-learning processes may include classification algorithms as defined above.

With further reference to FIG. 10, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 10, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 10, machine learning processes may include at least an unsupervised machine-learning processes 1032. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 1032 may not require a response variable; unsupervised processes 1032 may be used to find interesting patterns and/or inferences between variables, to determine a degree of correlation between two or more variables, or the like.

Still referring to FIG. 10, machine-learning module 1000 may be designed and configured to create a machine-learning model 1024 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 10, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 10, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 10, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 10, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 10, one or more processes or algorithms described above may be performed by at least a dedicated hardware unit 1036. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 1036 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 1036 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 1036 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 11:
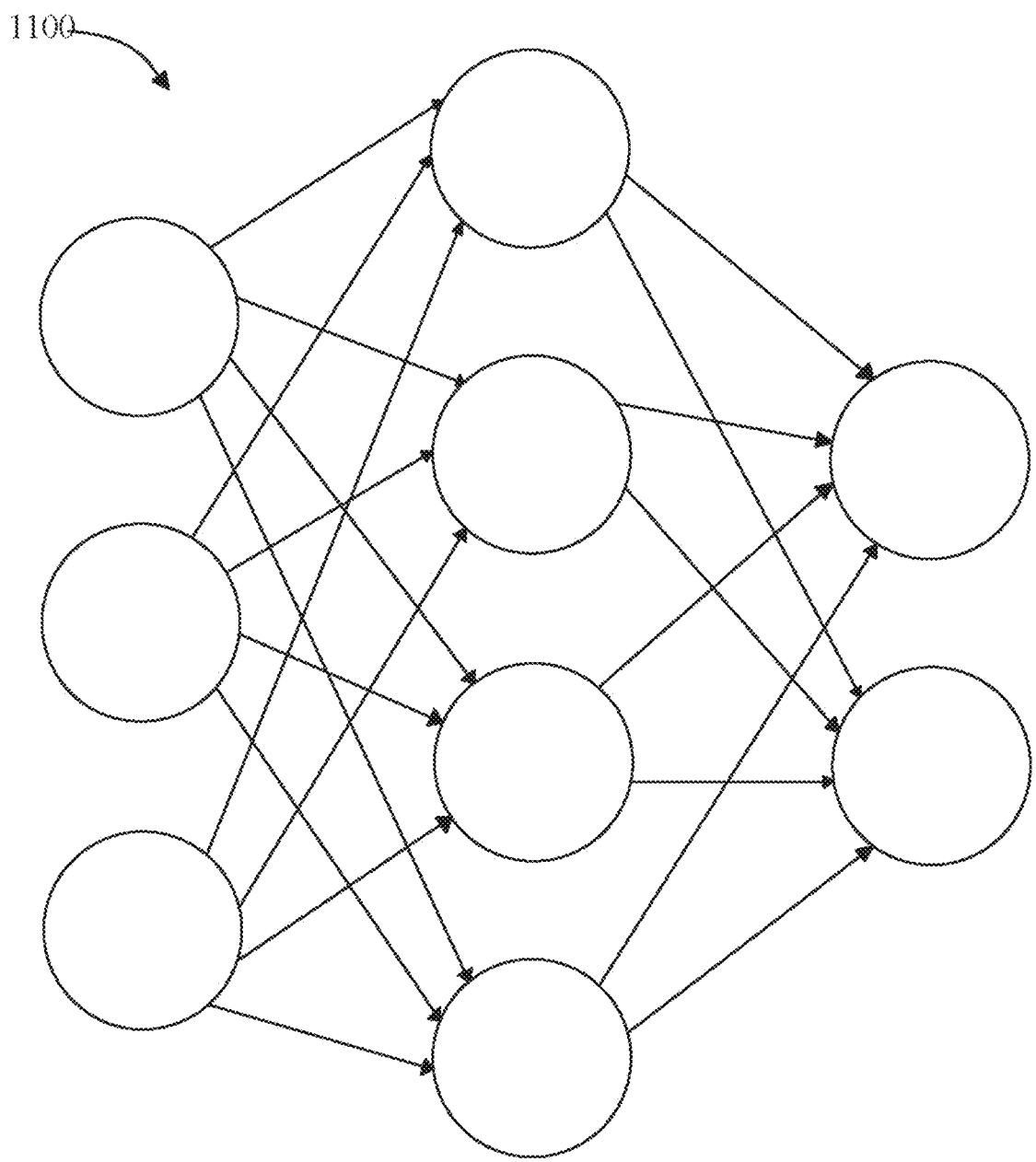
FIG. 11 illustrates a diagram of an exemplary nodal network.

Referring now to FIG. 11, an exemplary embodiment of neural network 1100 is illustrated. A neural network 1100 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 1104, one or more intermediate layers 1108, and an output layer of nodes 1112. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 12:
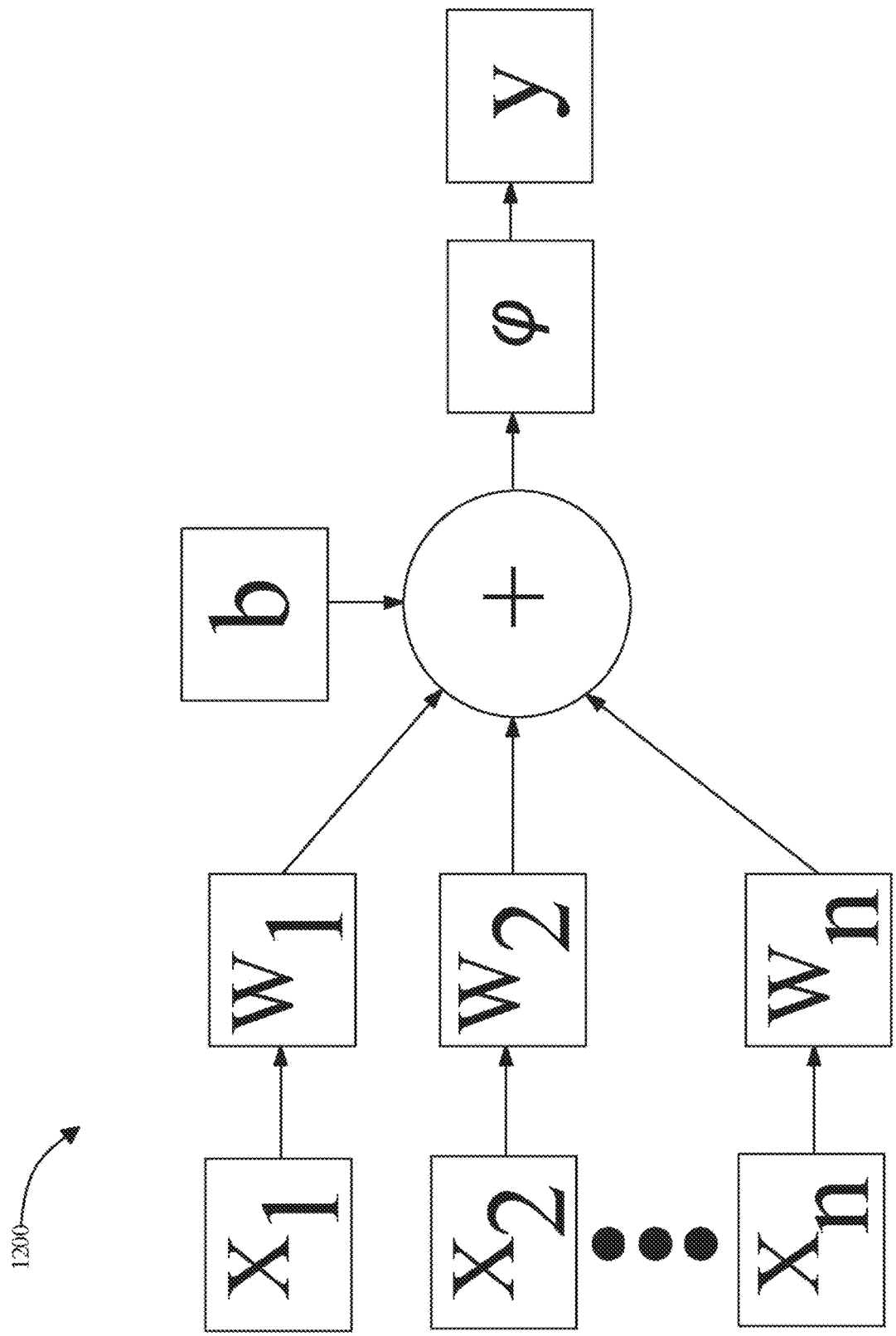
FIG. 12 illustrates a block diagram of an exemplary node.

Referring now to FIG. 12, an exemplary embodiment of a node 1200 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\Sigma_i x_i}$$

where the inputs to an instant layer are $x_i$, a swish function such as $f(x)=x*\text{sigmoid}(x)$, a Gaussian error linear unit function such as $f(x)=\alpha(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Computing device includes a processor. Processor may include, without limitation, any processor described in this disclosure. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device may include a single computing device operating independently, or may include two or more computing device operating in concert, in parallel, sequentially or the like; two or more computing devices may be included together in a single computing device or in two or more computing devices. computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device may include but is not limited to, for example, a computing device or cluster of computing devices in a first location and a second computing device or cluster of computing devices in a second location. computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. computing device may be implemented, as a non-limiting example, using a "shared nothing" architecture.

Computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Figure 13:
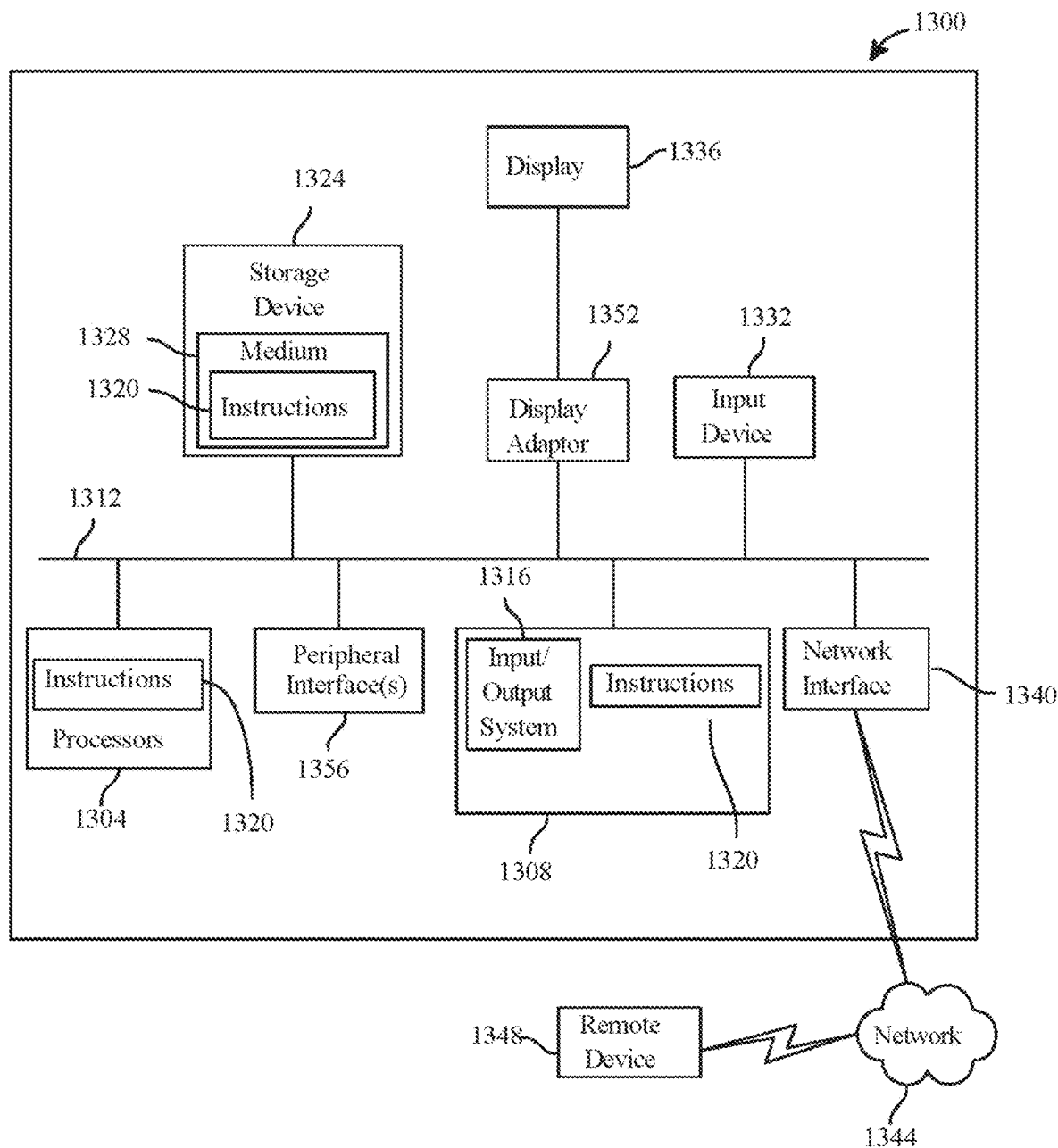
FIG. 13 illustrates a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A composition for a fecal derived sterilized postbiotic for anti-aging, the composition comprising:
   a plurality of dose schedules, wherein a dose schedule of the plurality of dose schedules is selected as a function of a baseline biomarker of aging measurement to be administered to a subject, wherein the baseline biomarker of aging measurement comprises a biomarker of aging;
   a plurality of biological macromolecules comprising at least an inorganic cofactor and a short chain fatty acid, wherein the short chain fatty acid comprises acetic acid, propionic acid, and butyric acid; and
   a plurality of agents, wherein the plurality of agents is configured to regulate the biomarker of aging, wherein the plurality of agents comprises at least a co-emulsifying agent, wherein the at least a co-emulsifying agent comprises at least a surfactant.

2. The composition of claim 1, wherein the baseline biomarker of aging measurement comprises a baseline biomarker of neurodegeneration.

3. The composition of claim 1, wherein the biomarker of aging comprises an epigenetic marker, wherein the epigenetic marker comprises a methylation marker.

4. The composition of claim 1, wherein the plurality of agents is configured to regulate heart rate variability.

5. The composition of claim 1, wherein the plurality of agents is configured to activate 5' AMP-activated protein kinase.

6. The composition of claim 1, wherein the composition is configured to reduce oxidative stress.

7. The composition of claim 1, wherein the composition is configured to increase healthspan.

8. The composition of claim 1, wherein the composition is configured to treat neurological disorders.

9. The composition of claim 1, wherein the composition is configured to change the baseline biomarker of aging measurement, wherein the change is analyzed using mRNA sequencing.

10. A method of reversing the impact of aging using a composition for a fecal derived sterilized postbiotic for antiaging, the method comprising:

obtaining a baseline biomarker of aging measurement, wherein the baseline biomarker of aging measurement comprises a biomarker of aging;

selecting a dose schedule from a plurality of dose schedules of a composition for a fecal derived sterilized postbiotic as a function of the baseline biomarker of aging measurement, wherein the composition comprises:

a plurality of biological macromolecules comprising an inorganic cofactor and a at least a short chain fatty acid, wherein the short chain fatty acid comprises acetic acid, propionic acid, and butyric acid; and a plurality of agents, wherein the plurality of agents is configured to regulate the biomarker of aging wherein the plurality of agents comprises at least a co- emulsifying agent, wherein the at least a co-emulsifying agent comprises at least a surfactant; and administering the composition to a subject.

11. The method of claim 10, wherein the baseline biomarker of aging measurement comprises a baseline biomarker of neurodegeneration.

12. The method of claim 10, wherein the biomarker of aging comprises an epigenetic marker, wherein the epigenetic marker comprises a methylation marker.

13. The method of claim 10, wherein the plurality of agents is configured to regulate heart rate variability.

14. The method of claim 10, wherein the plurality of agents comprises a co- emulsifying agent.

15. The method of claim 10, wherein the plurality of agents is configured to activate 5' AMP-activated protein kinase.

16. The method of claim 10, wherein the composition is configured to reduce oxidative stress.

17. The method of claim 10, wherein the composition is configured to increase healthspan.

18. The method of claim 10, wherein the composition is configured to treat neurological disorders.

19. The method of claim 10, further comprising:

analyzing a change in the baseline biomarker of aging of the subject using mRNA sequencing.

\* \* \* \* \*